(12) United States Patent
Fougere

(10) Patent No.: US 11,622,751 B2
(45) Date of Patent: Apr. 11, 2023

(54) DEVICES AND METHODS FOR COLLECTING SALIVA SAMPLES FROM THE ORAL CAVITY

(71) Applicant: Johnson & Johnson Consumer Inc., Skillman, NJ (US)

(72) Inventor: Richard Fougere, Washington Crossing, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1120 days.

(21) Appl. No.: 16/225,800

(22) Filed: Dec. 19, 2018

(65) Prior Publication Data

US 2020/0196994 A1    Jun. 25, 2020

(51) Int. Cl.

| | | |
|---|---|---|
| *A61B 10/00* | (2006.01) | |
| *A61C 17/06* | (2006.01) | |
| *A61C 17/22* | (2006.01) | |
| *A61C 17/02* | (2006.01) | |
| *A61C 19/06* | (2006.01) | |
| *G01N 33/487* | (2006.01) | |

(52) U.S. Cl.
CPC ...... *A61B 10/0051* (2013.01); *A61B 10/0096* (2013.01); *A61C 17/02* (2013.01); *A61C 19/066* (2013.01); *G01N 33/487* (2013.01)

(58) Field of Classification Search
CPC .. A61N 1/0548; A61N 1/0428; A61C 17/228; A61C 17/0217; A61C 17/221
See application file for complete search history.

(56) References Cited

U.S. PATENT DOCUMENTS

| | | |
|---|---|---|
| 1,500,107 A | 7/1924 | Chandler |
| 3,379,192 A | 4/1968 | Warren, Jr. |
| 3,489,141 A | 1/1970 | Warren, Jr. |
| 3,516,402 A | 6/1970 | Toth |

(Continued)

FOREIGN PATENT DOCUMENTS

| | | |
|---|---|---|
| CN | 2356653 | 1/2000 |
| CN | 1476314 A | 2/2004 |

(Continued)

OTHER PUBLICATIONS

Int'l. Search Report PCT/IB2019/060000 dated Feb. 21, 2020.

(Continued)

*Primary Examiner* — Jon Eric C Morales

(57) ABSTRACT

Provided are methods for collecting saliva from the oral cavity of a mammal comprising: placing a mouthpiece of a device comprising the mouthpiece in the oral cavity of a mammal, the mouthpiece comprising a chamber defined by front and rear inner walls and a base inner wall of the mouthpiece, each of the front and rear inner walls of the chamber comprising a plurality of openings, and a switch disposed in the mouthpiece; and the device further comprising a saliva collection reservoir, a fluid supply reservoir, a pump, and means for directing fluid through said device; activating the switch disposed in the mouthpiece to pump saliva from the oral cavity to the saliva collection reservoir for collection; deactivating the pumping of saliva to the saliva collection reservoir; and subsequently pumping fluid from the fluid supply reservoir to the mouthpiece for cleaning or treatment of the oral cavity.

4 Claims, 8 Drawing Sheets

(56) References Cited

U.S. PATENT DOCUMENTS

| | | |
|---|---|---|
| 3,566,869 A | 3/1971 | Crowson |
| 3,675,459 A | 7/1972 | Dohmann |
| 3,731,675 A | 5/1973 | Kelly |
| 3,840,992 A | 10/1974 | English |
| 4,017,373 A | 4/1977 | Shaw |
| 4,071,956 A | 2/1978 | Andress |
| 4,106,501 A | 8/1978 | Ozbey et al. |
| 4,148,309 A | 4/1979 | Reibel |
| 4,164,940 A | 8/1979 | Quinby |
| 4,170,230 A | 10/1979 | Nelson |
| 4,237,574 A | 12/1980 | Kelly et al. |
| 4,291,017 A | 9/1981 | Beierle et al. |
| 5,029,576 A | 7/1991 | Evans, Sr. |
| 5,030,098 A | 7/1991 | Branford |
| 5,046,491 A | 9/1991 | Derrick |
| 5,104,315 A | 4/1992 | McKinley |
| 5,137,039 A | 11/1992 | Klinkhammer |
| 5,177,827 A | 1/1993 | Ellison |
| 5,355,893 A | 10/1994 | Mick |
| 5,365,624 A | 11/1994 | Berns |
| 5,443,386 A | 8/1995 | Viskup |
| 5,458,487 A | 10/1995 | Komatsu |
| 5,465,728 A | 11/1995 | Phillips |
| 5,509,801 A | 4/1996 | Nicholson |
| 5,513,986 A | 5/1996 | Feltham |
| 5,570,709 A | 11/1996 | Haddad et al. |
| 5,616,028 A | 4/1997 | Hafele et al. |
| 5,950,624 A | 9/1999 | Hart |
| 5,980,498 A | 11/1999 | Brown |
| 6,022,326 A | 2/2000 | Tatum |
| 6,126,444 A | 10/2000 | Horiguchi |
| 6,152,733 A | 11/2000 | Hegemann et al. |
| 6,155,824 A | 12/2000 | Kamen et al. |
| 6,174,164 B1 | 1/2001 | Masjedi |
| 6,203,320 B1 | 3/2001 | Williams et al. |
| 6,224,376 B1 | 5/2001 | Cloonan |
| 6,353,956 B1 | 3/2002 | Berge |
| 6,375,459 B1 | 4/2002 | Kamen et al. |
| 6,468,222 B1 | 10/2002 | Mault |
| 6,599,253 B1 | 7/2003 | Baum |
| 6,602,071 B1 | 8/2003 | Ellion et al. |
| 6,893,259 B1 | 5/2005 | Reizenson |
| 6,899,684 B2 | 5/2005 | Mault |
| 6,935,857 B1 | 8/2005 | Farrell |
| 7,118,377 B2 | 10/2006 | Inoue et al. |
| 7,364,551 B2 | 4/2008 | Allen |
| 7,837,939 B2 | 11/2010 | Tung et al. |
| 7,935,065 B2 | 5/2011 | Martin |
| 7,972,277 B2 | 7/2011 | Oki |
| 9,308,064 B2 | 4/2016 | Binner et al. |
| 9,968,335 B2 | 5/2018 | Binner et al. |
| 2002/0082544 A1 | 6/2002 | Thrash et al. |
| 2003/0143511 A1 | 7/2003 | Trichas |
| 2003/0153844 A1 | 8/2003 | Smith |
| 2003/0233086 A1 | 12/2003 | Burns |
| 2004/0045107 A1 | 3/2004 | Egeresi |
| 2004/0082878 A1 | 4/2004 | Baldwin |
| 2004/0087874 A1 | 5/2004 | Schneider |
| 2004/0106081 A1 | 6/2004 | Karazivan et al. |
| 2004/0146836 A1 | 7/2004 | Andersen |
| 2004/0193235 A1 | 9/2004 | Altshuler et al. |
| 2004/0236244 A1 | 11/2004 | Allen |
| 2005/0037315 A1 | 2/2005 | Inoue et al. |
| 2005/0096563 A1 | 5/2005 | Liang |
| 2005/0136376 A1 | 6/2005 | Yeh |
| 2005/0196725 A1 | 9/2005 | Fu |
| 2005/0272002 A1 | 12/2005 | Chenvainu et al. |
| 2006/0078844 A1 | 4/2006 | Goldman et al. |
| 2006/0188841 A1 | 8/2006 | Edel et al. |
| 2006/0278238 A1 | 12/2006 | Borody |
| 2006/0292521 A1 | 12/2006 | Hegemann |
| 2007/0039614 A1 | 2/2007 | Djupesland |
| 2007/0106138 A1 | 5/2007 | Beiski |
| 2007/0140777 A1 | 6/2007 | Brunson |
| 2007/0184404 A1 | 8/2007 | Johnki |
| 2007/0254260 A1 | 11/2007 | Alden |
| 2008/0131844 A1 | 6/2008 | Taylor |
| 2008/0182218 A1 | 7/2008 | Chen |
| 2008/0199831 A1 | 8/2008 | Teichert et al. |
| 2008/0213843 A1 | 9/2008 | Nielsen |
| 2008/0216843 A1 | 9/2008 | Jiang |
| 2008/0280251 A1 | 11/2008 | Gallagher |
| 2009/0024058 A1 | 1/2009 | Blowick et al. |
| 2009/0029058 A1 | 1/2009 | Grasboeck |
| 2009/0038615 A1 | 2/2009 | Bradley |
| 2009/0123886 A1 | 5/2009 | Vaska |
| 2009/0136893 A1 | 5/2009 | Zegarelli |
| 2009/0208898 A1 | 8/2009 | Kaplan |
| 2010/0004555 A1 | 1/2010 | Bazemore |
| 2010/0016908 A1 | 1/2010 | Martin |
| 2010/0055634 A1 | 3/2010 | Spaulding et al. |
| 2010/0242193 A1 | 9/2010 | Harrison et al. |
| 2010/0311007 A1 | 12/2010 | Eliyahov |
| 2010/0312133 A1 | 12/2010 | Bazemore |
| 2010/0330538 A1 | 12/2010 | Salazar et al. |
| 2011/0015543 A1 | 1/2011 | Butlin |
| 2011/0021942 A1 | 1/2011 | Choe |
| 2011/0027746 A1 | 2/2011 | McDonough et al. |
| 2011/0027747 A1 | 2/2011 | Fougere et al. |
| 2011/0027748 A1 | 2/2011 | Fusi, II |
| 2011/0027758 A1 | 2/2011 | Ochs |
| 2011/0136070 A1 | 6/2011 | Rubin et al. |
| 2011/0213328 A1 | 9/2011 | Martin |
| 2011/0294096 A1 | 12/2011 | DeCastro et al. |
| 2011/0318705 A1 | 12/2011 | Sullivan |
| 2012/0021375 A1 | 1/2012 | Binner |
| 2012/0021376 A1 | 1/2012 | Iwamoto |
| 2012/0123225 A1 | 5/2012 | Al-Tawil |
| 2012/0219926 A1 | 8/2012 | Sullivan et al. |
| 2013/0023797 A1 | 1/2013 | Hanewinkel |
| 2013/0211270 A1 | 8/2013 | St. Laurent |
| 2015/0072300 A1* | 3/2015 | Wolpo ............... A61C 17/0217 433/32 |

FOREIGN PATENT DOCUMENTS

| | | |
|---|---|---|
| CN | 101035485 A | 9/2007 |
| CN | 101076298 A | 11/2007 |
| CN | 103327931 A | 9/2013 |
| DE | 202004010101 U1 | 11/2005 |
| EP | 101618 A | 2/1984 |
| EP | 688542 A | 12/1995 |
| EP | 761181 A | 3/1997 |
| EP | 1525857 A | 4/2005 |
| EP | 2822501 A1 | 1/2015 |
| FR | 2455456 A | 11/1980 |
| JP | 59125556 A | 7/1984 |
| JP | 2299651 A | 12/1990 |
| JP | 6217996 A | 8/1994 |
| JP | 7047088 A | 2/1995 |
| JP | 7-15004 | 3/1995 |
| JP | 11035435 A | 2/1999 |
| JP | 11309160 A | 11/1999 |
| JP | 2001-008736 A | 1/2001 |
| JP | 2001-120579 A | 5/2001 |
| JP | 2001-120627 A | 5/2001 |
| JP | 2002-045378 A | 2/2002 |
| JP | 2004-057315 A | 2/2004 |
| JP | 2004-230118 A | 8/2004 |
| JP | 2005-319254 A | 11/2005 |
| JP | 2005-334104 A | 12/2005 |
| JP | 2006-020887 A | 1/2006 |
| JP | 2006-101941 A | 4/2006 |
| JP | 2006-239368 A | 9/2006 |
| JP | 2008-501412 A | 1/2008 |
| JP | 2008-515575 | 5/2008 |
| KR | 20100138680 A | 12/2010 |
| KR | 101839344 B1 | 3/2018 |
| SU | 1024079 A | 6/1983 |
| WO | WO 96/07906 A1 | 3/1996 |
| WO | WO 2001/097709 A | 12/2001 |
| WO | WO 2003/039392 A | 5/2003 |
| WO | WO 2004/064666 A | 8/2004 |
| WO | WO 2004/108008 A | 12/2004 |

(56) References Cited

FOREIGN PATENT DOCUMENTS

| | | |
|---|---|---|
| WO | WO 2005/087133 A | 9/2005 |
| WO | WO 2005/107636 A | 11/2005 |
| WO | WO 2005/120387 A2 | 12/2005 |
| WO | WO 2006/040018 A1 | 4/2006 |
| WO | WO 2006/100452 A1 | 9/2006 |
| WO | WO 2006/119855 A | 11/2006 |
| WO | WO 2006/128021 A | 11/2006 |
| WO | WO 2007/071031 A | 6/2007 |
| WO | WO 2007/121760 A | 11/2007 |
| WO | WO 2008/016342 A | 2/2008 |
| WO | WO 2012/018555 | 2/2012 |
| WO | WO 2015/070688 A1 | 5/2015 |

OTHER PUBLICATIONS

U.S. Appl. No. 12/844,875, filed Jul. 28, 2010 (U.S. Pat. No. 8,684,956) McDonough et al.

U.S. Appl. No. 12/844,879, filed Jul. 28, 2010 (U.S. Pat. No. 8,617,090) Fougere et al.

U.S. Appl. No. 12/844,883, filed Jul. 28, 2010 (U.S. Pat. No. 9,022,959) Fusi II et al.

U.S. Appl. No. 12/844,885, filed Jul. 28, 2010 McDonough, et al. (Abandoned).

U.S. Appl. No. 13/188,018, filed Jul. 21, 2011 (U.S. Pat. No. 9,308,064) Binner, et al.

U.S. Appl. No. 15/054,008, filed Feb. 25, 2016 (U.S. Pat. No. 9,968,335) Binner, et al.

U.S. Appl. No. 13/314,257, filed Dec. 8, 2011 (U.S. Pat. No. 9,022,960) McDonough, et al.

U.S. Appl. No. 13/314,263, filed Dec. 8, 2011 (U.S. Pat. No. 9,022,961) McDonough, et al.

U.S. Appl. No. 13/353,487, filed Jan. 19, 2012 McDonough, et al. (Abandoned).

U.S. Appl. No. 13/413,760, filed Mar. 7, 2012 McDonough et al. (Abandoned).

U.S. Appl. No. 12/844,885, filed Jul. 28, 2010 Ochs, et al. (Abandoned).

U.S. Appl. No. 14/669,894, filed Mar. 26, 2015 (U.S. Pat. No. 9,668,839) McDonough, et al.

U.S. Appl. No. 14/674,541, filed Mar. 31, 2015 (U.S. Pat. No. 9,579,173) Fougere, et al.

U.S. Appl. No. 15/787,151, filed Oct. 18, 2017 (U.S. Pat. No. 11,123,167) McDonough, et al.

U.S. Appl. No. 14/088,746, filed Nov. 25, 2013 (U.S. Pat. No. 9,572,641) McDonough, et al.

U.S. Appl. No. 16/180,473, filed Nov. 5, 2018 (U.S. Pat. No. 11,135,043) Ochs, et al.

\* cited by examiner

DEVICES AND METHODS FOR COLLECTING SALIVA SAMPLES FROM THE ORAL CAVITY

FIELD OF THE INVENTION

The present invention relates to devices and methods suitable for in-home use to collect saliva samples from the oral cavity for analysis.

BACKGROUND OF THE INVENTION

Saliva testing is a diagnostic technique that involves analysis of saliva to identify markers of endocrine, immunologic, inflammatory, infectious, and other types of conditions. Saliva is a useful biological fluid for assaying steroid hormones such as cortisol, genetic material like RNA, proteins such as enzymes and antibodies, and a variety of other substances, including natural metabolites, including saliva nitrite, a biomarker for nitric oxide status, Saliva testing is used to screen for or diagnose numerous conditions and disease states, including Cushing's disease, anovulation, HIV, cancer, parasites, hypogonadism, and allergies.

Advantages of saliva include ease of collection, safety, non-invasiveness, affordability, and accuracy. Additionally, since multiple samples can be readily obtained, saliva testing is particularly useful for performing chronobiological assessments that span hours, days, or weeks.

Collecting large samples of whole saliva has a myriad of advantages. Large sample size collection allows the sample to be tested for more than one biomarker. Passive drooling is one way that large samples of whole saliva may be collected, as well as the use of saliva sample stimulating agents. Passive drooling, however, is time-consuming, and the use of saliva sample stimulating agents may increase the possibility of contamination of the sample.

Daily oral hygiene is generally recognized as an effective preventative measure against the onset, development, and/or exacerbation of periodontal disease, gingivitis and/or tooth decay. Unfortunately, however, even the most meticulous individuals dedicated to thorough brushing and flossing practices often fail to reach, loosen and remove deep-gum and/or deep inter-dental food particulate, plaque or biofilm. Most individuals have professional dental cleanings biannually to remove tarter deposits.

For many years products have been devised to facilitate the simple home cleaning of teeth, although as yet a single device which is simple to use and cleans all surfaces of a tooth and/or the gingival or sub-gingival areas simultaneously is not available. The conventional toothbrush is widely utilized, although it requires a significant input of energy to be effective and, furthermore, a conventional toothbrush cannot adequately clean the inter-proximal areas of the teeth. Cleaning of the areas between teeth currently requires the use of floss, pick, or some such other additional device apart from a toothbrush.

Electric toothbrushes inadequate to ensure proper inter-proximal tooth cleaning. Oral irrigators are known to clean the inter-proximal area between teeth. However, such devices have a single jet which must be directed at the precise inter-proximal area involved in order to remove debris. These water pump type cleaners are therefore typically only of significant value in connection with teeth having braces thereupon which often trap large particles of food. It will be appreciated that if both debris and plaque are to be removed from teeth, at present a combination of a number of devices must be used, which is extremely time consuming and inconvenient.

In addition, in order for such practices and devices to be effective, a high level of consumer compliance with techniques and/or instructions is required. The user-to-user variation in time, cleaning/treating formula, technique, etc., will affect the cleaning of the teeth.

In summary, saliva collection and testing is a safe, easy, non-invasiveness, affordable, and accurate diagnostic technique to evaluate the health of an individual. Simple methods of collecting large samples of whole saliva have a myriad of advantages. In addition, devices and methods for collecting whole saliva and ameliorating a detrimental condition or to improving cosmetic appearance of the oral cavity are needed.

SUMMARY OF THE INVENTION

According to one aspect are provided methods for collecting saliva from the oral cavity of a mammal comprising: placing a mouthpiece of a device comprising the mouthpiece in the oral cavity of a mammal, the mouthpiece comprising a chamber defined by front and rear inner walls and a base inner wall of the mouthpiece, each of the front and rear inner walls of the chamber comprising a plurality of openings, and a switch disposed in the mouthpiece; and the device further comprising a saliva collection reservoir, a fluid supply reservoir, a pump, and means for directing fluid through said device;

activating the switch disposed in the mouthpiece to pump saliva from the oral cavity to the saliva collection reservoir for collection;

deactivating the pumping of saliva to the saliva collection reservoir; and subsequently pumping fluid from the fluid supply reservoir to the mouthpiece for cleaning or treatment of the oral cavity.

BRIEF DESCRIPTION OF THE DRAWINGS

FIG. 7i is a cut-away view of the base station of the system of FIG. 7a;

DETAILED DESCRIPTION OF THE INVENTION

Figure 1:
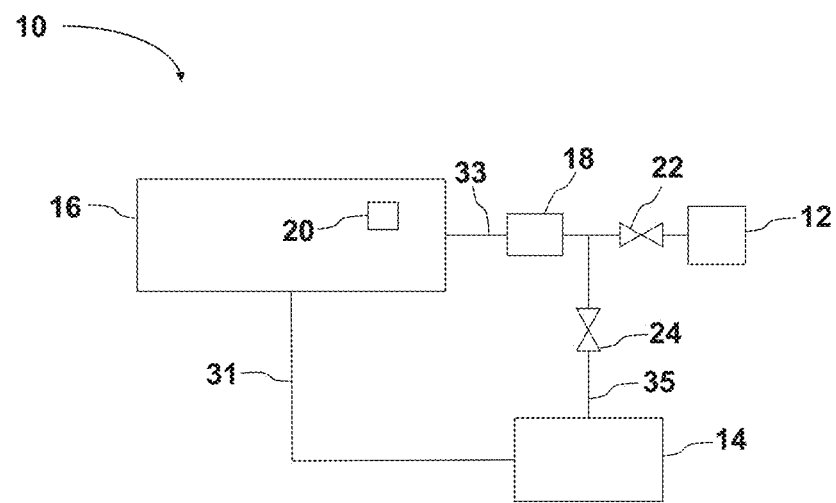
FIG. 1 is a schematic drawing of one embodiment of an apparatus that may be utilized in the present invention.

The present invention is directed to devices suitable for collecting saliva samples from the oral cavity of a mammal. The device includes an application tray, or mouthpiece, comprising a chamber for fitting around the teeth of the user and means for collecting the saliva sample from the oral cavity. In certain embodiments, the mouthpiece is suitable for directing a fluid onto a plurality of surfaces of the oral cavity. In such embodiments, the chamber maintains the fluid proximate the plurality of surfaces of the oral cavity and the front and rear inner walls include a plurality of openings. The mouthpiece includes a first manifold for containing a first portion of the fluid and providing the first portion to the chamber through the openings of the front inner wall, a second manifold for containing a second portion of the fluid and providing the second portion to the chamber through the openings of the rear inner wall, a first port for conveying the first portion of fluid to and from the first manifold, a second port for conveying the second portion of fluid to and from the second manifold. The mouthpiece further includes means for providing an effective seal of the mouthpiece within the oral cavity. The invention is further directed to methods of collecting and analyzing saliva samples from the oral cavity, including the steps of placing the device in the oral cavity, collecting the saliva samples and conducting an analysis of the saliva samples.

The terms "reciprocating movement of fluid(s)" and "reciprocation of fluid(s)" are used interchangeably herein. As used herein, both terms mean alternating the direction of flow of the fluid(s) back and forth over surfaces of the oral cavity of a mammal from a first flow direction to a second flow direction that is opposite the first flow direction.

By "effective fit or seal", it is meant that the level of sealing between the means for directing fluid onto and about the plurality of surfaces in the oral cavity, e.g. an application tray, is such that the amount of leakage of fluid from the tray into the oral cavity during use is sufficiently low so as to reduce or minimize the amount of fluid used and to maintain comfort of the user, e.g. to avoid choking or gagging. Without intending to be limited, gagging is understood to be a reflex (i.e. not an intentional movement) muscular contraction of the back of the throat caused by stimulation of the back of the soft palate, the pharyngeal wall, the tonsillar area or base of tongue, meant to be a protective movement that prevents foreign objects from entering the pharynx and into the airway. There is variability in the gag reflex among individuals, e.g. what areas of the mouth stimulate it. In addition to the physical causes of gagging, there may be a psychological element to gagging, e.g. people who have a fear of choking may easily gag when something is placed in the mouth.

As used herein, "means for conveying fluid" includes structures through which fluid may travel or be transported throughout the systems and devices according to the invention and includes, without limitation passages, conduits, tubes, ports, portals, channels, lumens, pipes and manifolds. Such means for conveying fluids may be utilized in devices for providing reciprocation of fluids and means for directing fluids onto and about surfaces of the oral cavity. Such conveying means also provide fluid to the directing means and provide fluid to the reciprocation means from a reservoir for containing fluid, whether the reservoir is contained within a hand-held device containing the reciprocation means or a base unit. The conveying means also provides fluid from a base unit to a fluid reservoir contained within the hand-held device.

Inventions described herein include methods and devices useful in collecting saliva samples from the oral cavity of a mammal, e.g. a human, for analysis and diagnostic purposes. Devices of the invention not only provide for collection of saliva, but also may provide a beneficial effect to the oral cavity, e.g. cleaning or treatment.

Use of a mouthpiece according to the invention provides the ability to sample consistently over a wider area of the oral cavity for a higher quality and more uniform diagnostic saliva sample, as well as providing consistent sample collection at specific sites in the oral cavity, as is described in more detail herein below. Devices and methods of the invention provide the advantage of preparing the saliva sample in-vivo, prior to, during, or after sampling. In certain embodiments, saliva sample stimulating agents and/or conglomeration agents that can provide a more consistent, higher quality saliva sample may be introduced prior to, during, or after collection of the saliva sample.

Certain methods entail collecting a saliva sample from the oral cavity for analysis and contacting a plurality of surfaces of the oral cavity with a fluid that is effective for providing the desired beneficial effect to the oral cavity. In such methods, reciprocation of the fluid(s) over the plurality of surfaces of the oral cavity is provided under conditions effective to provide the desired beneficial effect to the oral cavity. Contact of the plurality of surfaces by the fluid may be conducted substantially simultaneous. By substantially simultaneous, it is meant that, while not all of the plurality of surfaces of the oral cavity are necessarily contacted by the saliva at the same time, the majority of the surfaces are contacted simultaneously, or within a short period of time to provide an overall effect similar to that as if all surfaces are contacted at the same time. Collection of the saliva samples may be conducted prior to, or simultaneously with, or subsequent to contacting the surfaces of the oral cavity with fluid. In certain embodiments, collection may be conducted prior to, simultaneously with and subsequent to contacting the surfaces of the oral cavity with fluid.

The conditions for providing the desired beneficial effect in the oral cavity may vary depending on the particular environment, circumstances and effect being sought. The different variables are interdependent in that they create a specific velocity of the fluid. The velocity requirement may be a function of the formulation in some embodiments. For example, with change in the viscosity, additives, e.g. abrasives, shear thinning agents, etc., and general flow properties of the formulation, velocity requirements of the jets may change to produce the same level of efficacy. Factors which may be considered in order to provide the appropriate conditions for achieving the particular beneficial effect sought include, without limitation, the velocity and/or flow rate and/or pressure of the fluid stream, pulsation of the fluid, the spray geometry or spray pattern of the fluid, the temperature of the fluid and the frequency of the reciprocating cycle of the fluid.

The fluid pressures, i.e. manifold pressure just prior to exit through the jets, may be from about 0.5 psi to about 30 psi, or from about 3 to about 15 psi, or about 5 psi. Flow rate of fluid may be from about 10 ml/s to about 60 ml/s, or about 20 ml/s to about 40 ml/s. It should be noted that the larger and higher quantity of the jets, the greater flow rate required at a given pressure/velocity. Pulse frequency (linked to pulse length and delivery (ml/pulse), may be from about 0.5 Hz to about 50 Hz, or from about 5 Hz to about 25 Hz. Delivery pulse duty cycle may be from about 10% to 100%, or from about 40% to about 60%. It is noted that at 100% there is no pulse, but instead a continuous flow of fluid. Delivery pulse volume (total volume through all jets/nozzles) may be from about 0.2 ml to about 120 ml, or from about 0.5 ml to about 15 ml. Velocity of jetted pulse may be from about 4 cm/s to about 400 cm/s, or from about 20 cm/s to about 160 in/s. Vacuum duty cycle may be from about 10% to 100%, or from about 50% to 100%. It is noted that vacuum is always on at 100%. Volumetric delivery to vacuum ratio may be from about 2:1 to about 1:20, or from about 1:1 to 1:10.

The fluid(s) may include at least one ingredient, or agent, effective for providing the beneficial effect sought, in an amount effective to provide the beneficial effect when contacted with the surfaces of the oral cavity. For example, the fluid may be a liquid, where the liquid may include, without limitation, an ingredient selected from the group consisting of a cleaning agent, an antimicrobial agent, a mineralization agent, a desensitizing agent, surfactant and a whitening agent. In certain embodiments, more than one liquid may be used in a single session. For example, a cleaning solution may be applied to the oral cavity, followed by a second solution containing, for example, a whitening agent or an antimicrobial agent. Solutions also may include a plurality of agents to accomplish more than one benefit with a single application. For example, the solution may include both a cleansing agent and an agent for ameliorating a detrimental condition, as further discussed below. In addition, a single solution may be effective to provide more than one beneficial effect to the oral cavity. For example, the solution may include a single agent that both cleans the oral cavity and acts as an antimicrobial, or that both cleans the oral cavity and whitens teeth.

Liquids useful for improving the cosmetic appearance of the oral cavity may include a whitening agent to whiten teeth in the cavity. Such whitening agents may include, without limitation, hydrogen peroxide and carbamide peroxide, or other agents capable of generating hydrogen peroxide when applied to the teeth. Other whitening agents may include abrasives such as silica, sodium bicarbonate, alumina, apatites and bioglass.

It is noted that, while abrasives may serve to clean and/or whiten the teeth, certain of the abrasives also may serve to ameliorate hypersensitivity of the teeth caused by loss of enamel and exposure of the tubules in the teeth.

In some embodiments, the liquid may comprise an antimicrobial composition containing an alcohol having 3 to 6 carbon atoms. The liquid may be an antimicrobial mouthwash composition, particularly one having reduced ethanol content or being substantially free of ethanol, providing a high level of efficacy in the prevention of plaque, gum disease and bad breath. Noted alcohols having 3 to 6 carbon atoms are aliphatic alcohols. A particularly aliphatic alcohol having 3 carbons is 1-propanol.

In one embodiment the liquid may comprise an antimicrobial composition comprising (a) an antimicrobial effective amount of thymol and one or more other essential oils, (b) from about 0.01% to about 70.0% v/v, or about 0.1% to about 30% v/v, or about 0.1% to about 10% v/v, or about 0.2% to about 8% v/v, of an alcohol having 3 to 6 carbon atoms and (c) a vehicle. The alcohol may be 1-propanol. The liquid vehicle can be aqueous or non-aqueous, and may include thickening agents or gelling agents to provide the compositions with a particular consistency. Water and water/ethanol mixtures are the preferred vehicle.

Another embodiment of the liquid is an antimicrobial composition comprising (a) an antimicrobial effective amount of an antimicrobial agent, (b) from about 0.01% to about 70% v/v, or about 0.1% to about 30% v/v, or about 0.2% to about 8% v/v, of propanol and (c) a vehicle. The antimicrobial composition of this embodiment exhibits unexpectedly superior delivery system kinetics compared to prior art ethanolic systems. Exemplary antimicrobial agents which may be employed include, without limitation, essential oils, cetyl pyidium chloride (CPC), chlorhexidine, hexetidine, chitosan, triclosan, domiphen bromide, stannous fluoride, soluble pyrophosphates, metal oxides including but not limited to zinc oxide, peppermint oil, sage oil, sanguinaria, dicalcium dihydrate, aloe vera, polyols, protease, lipase, amylase, and metal salts including but not limited to zinc citrate, and the like. A particularly preferred aspect of this embodiment is directed to an antimicrobial oral composition, e.g. a mouthwash having about 30% v/v or less, or about 10% v/v or less, or about 3% v/v or less, of 1-propanol.

Yet another embodiment of the liquid is a reduced ethanol, antimicrobial mouthwash composition which comprises (a) an antimicrobial effective amount of thymol and one or more other essential oils; (b) from about 0.01 to about 30.0% v/v, or about 0.1% to about 10% v/v, or about 0.2% to about 8% v/v, of an alcohol having 3 to 6 carbon atoms; (c) ethanol in an amount of about 25% v/v or less; (d) at least one surfactant; and (e) water. Preferably the total concentration of ethanol and alcohol having 3 to 6 carbon atoms is no greater than 30% v/v, or no greater than 25% v/v, or no greater than 22% v/v.

In still another embodiment, the liquid is an ethanol-free antimicrobial mouthwash composition which comprises (a) an antimicrobial effective amount of thymol and one or more other essential oils; (b) from about 0.01% to about 30.0% v/v, or about 0.1% to about 10% v/v, or about 0.2% to about 8%, of an alcohol having 3 to 6 carbon atoms; (c) at least one surfactant; and (d) water.

The alcohol having 3 to 6 carbon atoms is preferably selected from the group consisting of 1-propanol, 2-propanol, 1-butanol, 2-butanol, tert-butanol and corresponding diols. 1-Propanol and 2-propanol are preferred, with 1-propanol being most preferred.

In addition to generally improving the oral hygiene of the oral cavity by cleaning, for example, removal or disruption of plaque build-up, food particles, biofilm, etc., the inventions are useful to diagnose and ameliorate detrimental conditions within the oral cavity and to improve the cosmetic appearance of the oral cavity. Detrimental conditions may include, without limitation, caries, gingivitis, inflammation, symptoms associated with periodontal disease, halitosis, sensitivity of the teeth and fungal infection. The liquids themselves may be in various forms, provided that they have the flow characteristics suitable for use in devices and methods of the present invention. For example, the liquids may be selected from the group consisting of solutions, emulsions and dispersions. In certain embodiments, the liquid may comprise a particulate, e.g. an abrasive, dispersed in a liquid phase, e.g. an aqueous phase. In such cases, the abrasive would be substantially homogeneously dispersed in the aqueous phase in order to be applied to the surfaces of the oral cavity. In other embodiments, an oil-in-water or water-in-oil emulsion may be used. In such cases, the liquid will comprise a discontinuous oil phase substantially homogeneously dispersed within a continuous aqueous phase, or a discontinuous aqueous phase substantially homogenously dispersed in a continuous oil phase, as the case may be. In still other embodiments, the liquid may be a solution whereby the agent is dissolved in a carrier, or where the carrier itself may be considered as the agent for providing the desired beneficial effect, e.g., an alcohol or alcohol/water mixture, usually having other agents dissolved therein.

The present invention includes devices, e.g. an oral hygiene device, for example a dental cleaning apparatus, suitable for in-home use and adapted to collect saliva samples from the oral cavity and to direct fluid onto a plurality of surfaces of a tooth and/or the gingival area. In certain embodiments the surfaces of the oral cavity are contacted by the fluid substantially simultaneously. As used herein, reference to the gingival area includes, without limitation, reference to the sub-gingival pocket. The appropriate fluid is directed onto a plurality of surfaces of teeth and/or gingival area substantially simultaneously in a reciprocating action under conditions effective to provide cleaning, and/or general improvement of the cosmetic appearance of the oral cavity and/or amelioration of a detrimental condition of the teeth and/or gingival area, thereby providing generally improved oral hygiene of teeth and/or gingival area. For example, one such device cleans teeth and/or the gingival area and removes plaque using an appropriate cleaning fluid by reciprocating the fluid back and forth over the front and back surfaces and inter-proximal areas of the teeth, thereby creating a cleaning cycle while minimizing the amount of cleaning fluid used.

Devices of the invention that provide reciprocation of the fluid comprise a means for controlling reciprocation of the fluid. The controlling means include means for conveying the fluid to and from a means for directing the fluid onto the plurality of surfaces of the oral cavity. In certain embodiments, the means for providing reciprocation of the fluid comprises a plurality of portals for receiving and discharging the fluid, a plurality of passages, or conduits, through which the fluid is conveyed, and means for changing the direction of flow of the liquid to provide reciprocation of the fluid, as described in more detail herein below. The controlling means may be controlled by a logic circuit and/or a mechanically controlled circuit.

In certain embodiments, devices for providing reciprocation may include a means for attaching or connecting the device to a reservoir for containing the fluid. The reservoir may be removably attached to the device. In this case, the reservoir and the device may comprise means for attaching one to the other. After completion of the process, the reservoir may be discarded and replaced with a different reservoir, or may be refilled and used again. In other embodiments, the reciprocating device will include a reservoir integral with the device. In embodiments where the device may be attached to a base unit, as described herein, the reservoir, whether integral with the device or removably attached to the device, may be refilled from a supply reservoir which forms a part of the base unit. Where a base unit is utilized, the device and the base unit will comprise means for attaching one to the other.

The device will comprise a power source for driving the means for reciprocating fluids. The power source may be contained within the device, e.g. in the handle of the device, for example, batteries, whether rechargeable or disposable. Where a base unit is employed, the base may include means for providing power to the device. In other embodiments, the base unit may include means for recharging the rechargeable batteries contained within the device.

Devices for providing reciprocation of fluids will include means for attaching the device to means for directing the fluid onto the plurality of surfaces of the oral cavity, e.g. an application tray or mouthpiece. In certain embodiments, the directing means provides substantially simultaneous contact of the plurality of surfaces of the oral cavity by the liquid. The attachment means may provide removable attachment of the mouthpiece to the device. In such embodiments, multiple users may use their own mouthpiece with the single device comprising the reciprocating means. In other embodiments, the attachment means may provide a non-removable attachment to the mouthpiece, whereby the mouthpiece is an integral part of the device. Devices for providing reciprocation as described above may be contained within a housing with other device components so as to provide a hand-held device suitable for providing fluid to the directing means, as described herein below.

The means for directing the fluid onto the surfaces of the oral cavity, e.g. an application tray or mouthpiece, is comprised of multiple components. The directing means comprises a chamber for maintaining the fluid proximate the plurality of surfaces, i.e. liquid-contacting-chamber (LCC). By "proximate", it is meant that the fluid is maintained in contact with the surfaces. The LCC is defined by the space bounded by the front inner wall and rear inner wall of the mouthpiece, and a wall, or membrane, extending between and integral with the front and rear inner walls of the mouthpiece, and in certain embodiments, a rear gum-sealing membrane. Together, the front and rear inner walls, the wall extending there between and rear gum-sealing membrane form the liquid-contacting-chamber membrane (LCCM). The general shape of the LCCM is that of a "U" or an "n", depending on the orientation of the mouthpiece, which follows the alignment of the teeth to provide uniform and optimized contact by the liquid. The LCCM may be flexible or rigid depending on the particular directing means. The membrane may be located as a base membrane of the LCCM. The front and rear inner walls of the LCCM each include a plurality of openings, or slots, through which the liquid is directed to contact the plurality of surfaces of the oral cavity.

The LCCM design may be optimized for maximum effectiveness as it relates to the size, shape, thickness, materials and volume created around the teeth/gingiva, nozzle design and placement as it relates to the oral cavity and the teeth in conjunction with the manifold and gingival margin seal to provide comfort and minimize the gagging reflex of the user. The combination of the above provides effective contact of the teeth and gingival area by the liquid.

The LCCM provides a controlled and isolated environment with known volume, i.e. the LCC, to contact teeth and/or gingival area with liquids, and then to remove spent liquids, as well as debris, plaque, etc., from the LCC without exposing the whole oral cavity to liquid, debris, etc. This decreases the potential for ingestion of the liquids. The LCCM also allows increased flow rates and pressure of liquids without drowning the individual nozzles when significant flow rates are required to provide adequate cleaning, for example. The LCCM also allows reduced liquid quantities and flow rates when required, as only the area within the LCC is being contacted with liquid, not the entire oral cavity. The LCCM also allows controlled delivery and duration of contact of liquid on, through and around teeth and the gingival area, allowing increased concentrations of liquids on the area being contacted by the liquid, thereby providing more effective control and delivery of liquid.

The LCCM may also allow controlled sampling of the oral cavity due to precise positioning of the mouthpiece in the oral care cavity for use in detection or diagnostics. It can also provide capability to image and/or diagnose gum health through a variety of methods. The system also provides the ability to expand functionality for cleaning and/or treating other oral cavity areas such as, but not limited to, the tongue, cheeks, gingival, etc.

In use, saliva samples are collected from the oral cavity for diagnostic analysis. Advantages of controlled sampling of the oral cavity may include real-time analysis and feedback to the user, consistent sampling due to the mouthpiece, and the ability to create a baseline of oral cavity conditions for the user and automatically analyze trends over time for personalized analysis. The mouthpiece provides an excellent opportunity for consistent collection of samples saliva in the oral cavity. By "consistent collection", it is meant that the collection of saliva, and thus the saliva samples, are unaffected by compliance or the technique employed by the user. The mouthpiece may be secured in the user's mouth in the same fashion every time, thus placing the means for collecting the saliva sample in the same location for every sample collection. In addition, the collection environment may be consistent and controlled every time. In certain embodiments, the sampling environment and/or location may be confirmed via feedback from sensor(s) placed in the mouthpiece.

The user may benefit from routine and regular tests to understand their personal baseline, as many diagnostic tests vary from one individual to another. The user's baseline may be determined over time, allowing a thorough and proper analysis through each use of the system.

A variety of beneficial diagnostic analyses may be performed using saliva from the oral cavity. Though many collection methods for saliva exist in the art, these often require professional training with proper technique to collect the correct quantity of the desired saliva. The sample must then be analyzed in a secondary process. The mouthpiece discussed here allows for consistent collection of saliva for repeatable analysis.

Devices in this invention are designed to initially collect fresh saliva prior to the initiation of the cleaning/treatment process. This is accomplished by having a switch disposed in or on the application tray (mouthpiece) at a location sensitive to a biting motion. In use, the mouthpiece is first inserted into the mouth. The user bites down on the mouthpiece activating the switch to initiate the collection of saliva from the oral cavity.

In some embodiments, the user repeatedly bites down on the mouthpiece in a chewing motion. Chewing is known to stimulate the production of saliva in the oral cavity, thereby yielding a greater amount of fresh saliva. After a set number of bites, the collection of saliva is halted, and the cleaning/treatment process is initiated. The number of bites on the mouthpiece to switch the device over from saliva collection to cleaning/treatment is two or more, or three or more, or six or more, or eight or more, or ten or more.

In other embodiments, when the user first bites down on the mouthpiece, the switch activates the collection of saliva from the oral cavity, and also activates a timer. The user repeatedly bites down on the mouthpiece in a chewing motion to stimulate the production of saliva in the oral cavity. After a set time, the collection of saliva is halted, and the cleaning/treatment process is initiated. The time to switch the device over from saliva collection to cleaning/treatment is more than about two seconds, or more than about five seconds, or more than about ten seconds, or more than about fifteen seconds.

Each time the mouthpiece is inserted into the mouth, it is located in the same position. For saliva sampling, a plurality of nozzles are located throughout the oral cavity. As the system operates, cleaning/treating fluid may move through the appliance, into the oral cavity, and out of the oral cavity. As the saliva is moving through the oral cavity, it may mix with fluid and therefore move saliva through the system. The mixed solution may be analyzed in the device as it is functioning or stored for later analysis. If desired, several means may be used to increase saliva production and increase the percentage of saliva in the overall system saliva mixture. Methods include, but are not limited to, use of a salivation-inducing saliva during system operation, user exposure to specific saliva-inducing smells, electrical stimulation, ultrasonic stimulation, or mechanical stimulation.

Alternatively, a saliva mixture may be collected through a separate and/or specific manifold in the mouthpiece. Through any means of collection, the saliva may be collected before, during, or after the cleaning/treatment process, or any combination thereof.

The mouthpiece may also have a collection means that contacts the tongue to suck or absorb saliva from it. The probe or pad contacting the tongue may have one or more nozzles that pull a vacuum on the tongue to collect the saliva. Alternatively, the pad may absorb saliva and automatically extract the saliva in a secondary process, or otherwise analyze the saliva directly on the pad. As in the above techniques, this method is technique- and compliance-free for the user.

Saliva samples may be utilized as diagnostic samples for a number of oral health conditions and analyzed via a variety of diagnostic methods.

The device may diagnose caries risk through microfluidic immunoassays performed on saliva samples to detect proteinaceous antigens specific to *S. mutans* and/or *Lactobacillus* bacteria with fluorescence detection of output. The assay may be performed weekly or monthly, and a warning registered to the user if the levels of bacteria were to surpass the threshold for high caries risk. Alternatively, the device may measure the buffering capacity of the saliva using a series of absorbent pads embedded with pH indicators, as known in the art. An alert to the user may be triggered by low buffering capacity results, indicating a high risk for caries. As an additional alternative, the device may directly measure the concentration of fluoride ions in the saliva using a fluoride ion specific electrode. A baseline may be established by monitoring the fluoride ion concentration on a daily or weekly basis for a specified period of time. Any significant deviations from baseline concentration trends would trigger an alert to the user.

The device may use microfluidic immunoassays to analyze saliva samples for the presence of antigens specific to bacteria associated with gingivitis and periodontitis. The assay may be performed daily, weekly or monthly, with the data being recorded over time. Any adverse deviations from normal trends would alert the user to consult a dental professional for further evaluation.

Alternatively, the device may analyze saliva samples using a lateral flow technology (LFT) test. After collection, the sample may be mixed with a bacterial cell lysing agent and the resulting mixture applied to a lateral flow devise in the base station which may detect antigens specific to *S. mutans* for assessing carries risk as known in the art. The lateral flow device may also detect antigens specific to bacteria associated with gingivitis and/or periodontisis either alone or in combination with *S. mutans* antigens. It may also react with thiols in volatile sulfur compounds (VSCs), or detect antigens specific to VSC-producing bacteria to produce a detectable color change with the intensity of the color correlating with the concentration of VSCs present. The lateral flow test may be performed in the base station with refillable LFT strips either specific for a single condition, or strips that will detect a combination of antigens and/or chemistries for multiple oral conditions. Results may be assessed in the base station. Alternatively, the test may be performed externally, with the user applying the sample collected and prepared by the device to the LFT strip with test results read visually by the user as the appearance of a colored indicator or color change on the strip. Conversely, analysis of the strip can occur automatically through digital image analysis.

Alternatively, the device may analyze saliva samples to determine the prevalence of disease-associated bacteria within the entire population in the sample using quantitative Polymerase Chain Reaction (qPCR) analysis. The analysis may be performed within the device or base station using microfluidic techniques or, alternatively, the sample may be collected and contained within the device and sent to an outside laboratory for analysis. The analysis may be performed daily, weekly or monthly and a high number of *S. mutans* or Lactobacilli would trigger a warning to the user that they may be at risk for developing caries, whereas high counts of organisms associated with periodontitis would alert the user to a possible prevalence for gum disease. In each case the analysis could be performed daily, weekly or monthly and tracked over time to identify significant deviations from normal trends.

Alternatively, the device may analyze saliva samples using DNA-DNA hybridization techniques to determine the bacterial population profile of the sample. This information may be recorded daily, weekly or monthly and tracked over time to monitor changes in relative amounts of different bacteria in the entire population. Significant adverse population shifts would trigger a warning to the user for increased risk of disease onset or progression (such as high risk for caries or periodontal disease). The information may also be used to track the progress of disease treatment.

In each of these cases, the user would be highly unlikely or unable to perform the diagnostic test described, and most are not routinely practiced in dental offices. The mouthpiece may provide the added benefit of acquiring this information in a consistent manner on a regular basis, and may enable the user to closely monitor their oral health status and take any required corrective measures in a timely fashion.

The collection methods and diagnostic analysis discussed above may used in conjunction with one another, in any combination. Due to the flexibility of the system, collection of each sample only needs to occur when determined or pre-established, rather than during every use. For example, some samples may need to be taken only once a week, while others ideally may be taken one or more times a day. The system may automatically adjust the sampling plan as needed for each individual, based on results and predetermined criteria.

In addition to the oral health diagnostics as described above, the device can also be utilized and expanded to diagnose general health conditions and biomarkers related to systemic health, including but not limited to cancers, hypertension, diabetes, etc.

Combinations of different biomarkers and samples can be combined to provide a more robust analysis and diagnosis for specific conditions and provide improved results, such as using GCG and saliva samples, and/or checking multiple biomarkers that are linked to a specific condition. The presence of one biomarker might also automatically trigger sampling and analysis of other biomarkers to improve diagnostic results.

Diagnostic results can also be used to provide automated treatment for the condition, and/or direct the user to purchase a specific product to address a potential condition. The treatment could also be customized by adding appropriate additives to the cleaning formulation for a specific user depending on their diagnostic result. As an example, adding a antibacterial, halitosis reducing agent, sensitivity agent, whitening agent, fluoride, and/or any combination of these or other additives to treat an oral and/or systemic condition.

The thickness of the walls of the LCCM may be within a range of 0.2 mm to 1.5 mm, to provide necessary physical performance properties, while minimizing material content, and optimizing performance. The distance between the inner walls of the LCCM to the teeth may be from about 0.1 mm to about 5 mm, and more typically an average distance of about 2.5 mm to provide maximum comfort, while minimizing customization and LCC volume requirements.

The size and shape of the mouthpiece preferably utilizes three basic universal sizes (small, medium and large) for both the top and bottom teeth, but the design provides mechanisms to allow different levels of customization as required to ensure comfort and functionality to the individual user. The device may incorporate a switching mechanism, which would allow it to be operable only when in the correct position in the mouth. The mouthpiece may include both upper and lower sections to provide substantially simultaneous contact of the plurality of surfaces of the oral cavity by fluid. In an alternate embodiment the upper and lower sections may be cleaned utilizing a single bridge that could be used on the upper or lower teeth and gums of the user (first placed on one portion for cleaning, then subsequently placed over the other portion for cleaning).

The number and location of openings, also referred to herein as slots, jets or nozzles, contained within the inner walls of the mouthpiece through which the fluid is directed will vary and be determined based upon the circumstances and environment of use, the particular user and the beneficial effect being sought. The cross-sectional geometry of the openings may be circular, elliptical, trapezoidal, or any other geometry that provides effective contact of the surfaces of the oral cavity by the fluid. The location and number of openings may be designed to direct jets of fluid in a variety of spray patterns effective for providing the desired beneficial effect. Opening diameters may be from about 0.1 to about 3 mm, or from about 0.2 mm to about 0.8 mm, or about 0.5 mm, to provide effective cleaning and average jet velocities and coverage.

Optimal opening placement and direction/angles allows coverage of substantially all teeth surfaces in the area if the oral cavity to be contacted by fluid, including but not limited to interdental, top, side, back, and gingival pocket surfaces.

In alternate embodiments, the openings could be of different sizes and different shapes to provide different cleaning, coverage and spray patterns, to adjust velocities, density and fan patterns (full cone, fan, partial, cone, jet), or due to formulation consideration. Nozzles could also be designed to be tubular and or extend from the LCCM to provide directed spray, or act as sprinkler like mechanism to provide extended coverage across the teeth, similar to a hose sprinkler system. The nozzles are preferably integral to the inner walls of the LCCM and can be incorporated into the inner walls through any number of assembly or forming techniques known in the art (insert molded, formed in membrane through machining, injection molding, etc.).

The LCCM may be an elastomeric material such as ethylene vinyl acetate (EVA), thermoplastic elastomer (TPE), or silicone, to allow motion of the inner walls and provide a greater jet coverage area with minimal mechanics, reducing the volumetric flow requirements to achieve optimized performance, while providing a softer and more flexible material to protect the teeth if direct contact with the teeth is made. A flexible membrane may also provide acceptable fitment over a large range of users, due to its ability to conform to the teeth. Alternatively, the LCCM could be made of a rigid or semi-rigid material, such as but not limited to a thermoplastic.

It may be desirable, although not required, to have motion of the LCCM relative to the teeth. Movement of the LCCM, and subsequently the nozzle direction during the cleaning and/or treatment operation, provides increased coverage of the teeth/gums, while minimizing the number of nozzles/fluidic jets required to provide this coverage for cleaning and/or treatment. It also reduces the required overall fluid flow requirement, which reduces the total fluid requirement and overall device overhead as it relates to provide the appropriate flow, resulting in a smaller, lighter, and useable device. This motion also allows the device to provide a more universal fit for the user (same sized LCCM can be used for different users), while also allowing compensation for minor misplacement/orientation of the LCCM over the user's teeth/gums.

In some embodiments, motion of the LCCM is provided through pressurization, pulsation, and movement of fluid through the manifolds. In alternate embodiments, this motion can be achieved through vibration, sonic, or ultrasonic mechanism. This motion can also be provided through a separate network of tubes and/manifolds constructed within or attached to the LCC, which can be charged or discharged with fluid and/or air to create a desired motion of the membrane. In addition, motion of the LCCM may be the result of the motion of the user's jaw or teeth. In an alternate embodiment, the LCCM motion system can also include mechanically moving the LCCM via a track-like guided reciprocating motion, the track being created by the teeth. In another alternate embodiment, the desired LCCM motion can be created by using one or a multiple of linear motor systems, which allow sequential motion via multiple permanent magnet/coil pairs located in strategic locations on the mouthpiece to provide optimized cleaning and treatment sequences for directing jets and cleaning elements. In yet another alternative embodiment, motion may be created by shape memory materials or piezoelectrics.

In the preferred embodiment, the system provides pulsation through a variety of elements, including through the delivery manifold, channels, and nozzles, the vacuum manifolds, channels and nozzles, and through the reciprocation/reversal of flow, where the delivery channels become the vacuum channels, and the vacuum channels the delivery channels. Pulsation of the fluid results in a varying pressure of the fluid within the elements described creating the desired motion of the LCCM as described. The LCCM is designed to work with the fluid pulsation means provided to create the necessary motion and movement/direction of the nozzles in the X, Y and Z directions, through the combination of materials and design of the LCCM, while still providing the necessary performance required to minimize leakage into the oral cavity and without compromising structural integrity of the mouthpiece, including the LCCM.

The movement/pulsation of the elements can be coordinated or random. The pulsation can be provided at a fixed frequency, multiple frequencies, and/or out of phase for the individual elements to create the desired motion. It is not necessary to pulsate all of the elements at once. As an example, in some cases only the delivery elements may be required to be pulsated, while the vacuum is not pulsated.

In addition, the LCCM could include cleaning elements and/or spacers that would move relative to the LCCM to provide some effect to the teeth and/or gums. These cleaning elements and/or spacers can also be used to constrain the motion of the LCCM if required to maintain a minimum distance between the LCCM and teeth/and/or gums during motion and fitment of the device to the user. This provides a minimum distance between the nozzle located within the LCCM and the surface to be treated and cleaned, preventing a nozzle from being blocked, and preventing fluid delivery and/or removal. As the spacer is moving with the movement of the LCCM during cleaning and/or treatment, it does not prevent or inhibit cleaning and/or treatment of surfaces that are in direct contact with the spacer, as this engagement location on the surface is constantly changing. In addition, the motion of the spacer relative to the surface being cleaned/treated may have additional beneficial effect through cleaning and/or stimulation of the contact surface during the cleaning/treatment process, similar to a tooth brushing or gum massaging like action.

In an alternate embodiment, the LCCM could also include abrasive elements such as filaments, textures, polishing elements, additives (silica, etc.), and other geometric elements that could be used for other cleaning and/or treatment requirements as well as ensuring minimal distance between the teeth and LCCM for, but not limited to, treatment, cleaning, and positioning.

In some embodiments, the LCCM may contain a sensing means device, which determines if the mouthpiece is in the correct position over the teeth in the oral cavity and which will not allow the device to activate unless this position is verified through the sensor. Also, if the mouthpiece is moved or dislodged from this position during use, it will immediately stop functioning. An override switch can be incorporated during application tray cleaning.

The sensing means can be manual, as in a manual switch(s) such as a membrane switch, or other switches known in the art. Other contact and non-contact sensing means can also be used, such as ultrasonic, Hall (magnetic), frequency, pressure, capacitance, inductance, laser, optical and other sensing means and devices know in the art.

The sensing means would be located in the appliance in such a way that it would measure change or provide a signal when the user positioned the mouthpiece in an acceptable position within the oral cavity, and enabling the device to operate the appropriate cycle.

An alternate and potentially redundant means of determining if the position and orientation of the mouthpiece is correct is to monitor the current and/or power required by the drive motor(s). If the current is above the acceptable range, it is an indication that the mouthpiece may be positioned incorrectly, either blocking delivery of the fluid or the removal/vacuum of fluid from the LCCM. If the current it too low, it is an indication that there is no restriction to vacuum or delivery flow, and again can be indicative of the mouthpiece not being in the correct position within the user's mouth, such as if the user accidently removed the device before the cleaning/treatment cycle was complete, or started the cycle when not positioned correctly within the oral cavity.

The LCCM could be created via a variety of methods such as, but not limited to, machining, injection molding, blow molding, extrusion, compression molding, and/or vacuum forming. It can also be created in conjunction with the manifold, but incorporating the manifold circuitry within the LCC, and/or over-molded onto the manifold to provide a unitary construction with minimal assembly.

In one embodiment, the LCCM may be fabricated separately and then assembled to the manifolds, utilizing any number of assembling and sealing techniques, including adhesives, epoxies, silicones, heat sealing, ultrasonic welding, and hot glue. The LCCM is designed in a way that, when assembled with the manifold, it effectively and efficiently creates the preferred dual manifold design without any additional components.

In certain embodiments, the LCCM can also be designed or used to create the gingival sealing area. In certain embodiments, a vacuum is applied within the LCC, which improves the engagement of the mouthpiece to form a positive seal with the gingival in the oral cavity. In other embodiments, a pressure is applied outside the LCCM, within the oral cavity, which improves the engagement of the mouthpiece to form a positive seal with the gingival in the oral cavity. In yet other embodiments, a denture-like adhesive may be applied around the mouthpiece during the initial use to provide a custom reusable resilient seal when inserted into the oral cavity for a particular user. It would then become resiliently rigid to both conform and provide a positive seal with the guns and on subsequent applications. In another embodiment, the seal could be applied and/or replaced or disposed of after each use.

The directing means also comprises a first manifold for containing the liquid and for providing the liquid to the LCC through the openings of the front inner wall, and a second manifold for containing the liquid and for providing the liquid to the chamber through the openings of the rear inner wall. This design provides a number of different options, depending on what operation is being conducted. For instance, in a cleaning operation, it may be preferable to deliver jets of liquid into the LCC directly onto the teeth from one side of the LCC from the first manifold and then evacuate/pull the liquid around the teeth from the other side of the LCC into the second manifold to provide controlled interdental, gumline and surface cleaning. This flow from the one side of the LCC could be repeated a number of times in a pulsing action before reversing the flow to deliver jets of liquid from the second manifold and evacuating/pulling the liquid through the back side of the teeth into the first manifold for a period of time and/or number of cycles. Such liquid action creates a turbulent, repeatable and reversible flow, thus providing reciprocation of the liquid about the surfaces of the oral cavity.

In a treatment, pre-treatment, or post-treatment operation it may be preferable to deliver the liquid through one or both manifolds simultaneously, flooding the chamber and submerging the teeth for a period of time and then evacuating the chamber after a set period of time through one or both manifolds.

In alternate embodiments, the manifold can be of single manifold design providing pushing and pulling of the liquid through the same sets of jets simultaneously, or can be any number of manifold divisions to provide even greater control of the liquid delivery and removal of the cleaning and liquid treatment. In the multi-manifold also can be designed to have dedicated delivery and removal manifolds. The manifolds can also be designed to be integral to and/or within the LCCM.

The material for the manifold would be a semi-rigid thermoplastic, which would provide the rigidity necessary not to collapse or burst during the controlled flow of the liquids, but to provide some flexibility when fitting within the user's mouth for mouthpiece insertion, sealing/position and removal. To minimize fabrication complexity, number of components and tooling cost, the dual manifold is created when assembled with the LCCM. The manifold could also be multi-component to provide a softer external "feel" to the teeth/gums utilizing a lower durometer elastomeric material, such as, but not limited to, a compatible thermoplastic elastomer (TPE). The manifold could be created via a variety of methods such as, but not limited to machining, injection molding, blow molding, compression molding, or vacuum forming.

The directing means also comprises a first port for conveying the liquid to and from the first manifold and a second port for conveying the liquid to and from the second manifold, and means for providing an effective seal of the directing means within the oral cavity, i.e. a gingival seal. In certain embodiments, the first and second ports may serve both to convey liquid to and from the first and second manifolds and to attach the mouthpiece to the means for providing liquid to the mouthpiece. In other embodiments, the directing means may further include means for attaching the directing means to means for providing liquid to the directing means.

FIG. 1 is a schematic drawing of an embodiment of a method and system according to the present invention. The system designed to initially collect fresh saliva prior to the initiation of the cleaning/treatment process. The figure shows system 10, with components including: a saliva collection reservoir 12, a fluid supply reservoir 14, a means for directing the fluid onto the plurality of surfaces of the oral cavity, in this instance shown as application tray or mouthpiece 16, pump 18, flow valves 22 and 24, and tubes 31, 33, and 35 for conveying the fluid throughout the system. Switch 20 is disposed in or on mouthpiece 16 to initiate the saliva collection and cleaning/treatment cycle. Tubes 35 tees into tube 33.

Pump 18 may be a piston pump, valveless rotary piston pump, diaphragm pump, peristaltic pump, gear pump, rotary pump, double-acting piston pump, vane pump, or similar. Fluid supply reservoir 14 may be made of glass, plastic or metal. Fluid supply reservoir 14 may be integral to system 10 and refillable. In some embodiments, fluid supply reservoir 14 may be a replaceable fluid supply, such as a single or multi-use cartridge, detachably connected to system 10.

In some embodiments, fluid supply reservoir 14 and/or tubes 31, 33, and 35 may include a heat source to pre-warm the fluid prior to direction into mouthpiece 16 for application to the surfaces of the oral cavity. The temperature should be maintained within a range effective to provide efficacy and comfort to the user during use.

Application tray 16, discussed in detail herein below, could be integral with, or detachably connected to system 10 by way of tubes 31, 33 and further attachment means (not shown). It could be one or two sided with internally, easily cleanable filters for trapping food particles. When positioned within the oral cavity, e.g. about the teeth and gums, mouthpiece 16 forms an effective fit or seal against the gums, and includes means to direct fluid against surfaces of the oral cavity, e.g. surfaces of the teeth.

During saliva collection, saliva collected in mouthpiece 16 flows through tube 33, pump 18, and flow valve 22 to saliva collection reservoir 12. During the cleaning/treatment cycle, fluid contained in the fluid supply reservoir 14 flows through tube 35, flow valve 24, tees into tube 31, and flows through pump 18 and into mouthpiece 16.

In some embodiments, during the cleaning/treatment cycle, fluid from mouthpiece 16 is returned to fluid supply reservoir 14 by flowing through tube 31. This allows for a smaller volume of cleaning/treatment fluid to be used by system 10.

In other embodiments, system 10 has means for providing reciprocation of fluid between fluid supply reservoir 14 and mouthpiece 16. In this embodiment, during the cleaning/treatment cycle, fluid contained in the liquid supply reservoir 14 flows through tube 35, flow valve 24, tees into tube 31, and flows through pump 18 and into mouthpiece 16, and is returned to fluid supply reservoir 14 by flowing through tube 31. Then, the direction of flow is reversed, and fluid contained in the fluid supply reservoir 14 flows through tube 31 and into mouthpiece 16, and is returned to fluid supply reservoir 14 by flowing through tube 31, pump 18, flow valve 24, and tube 35. In some embodiments, the direction of flow is reversed by reversing the flow direction of pump 18, such as with the use of a gear pump.

The saliva collection and cleaning/treatment actions of system 10 may be controlled by a logic circuit, which may include a program to start saliva collection when switch 20 is activated by a biting motion, and upon completion of saliva collection, the initiation of the cleaning/treatment cycle. In embodiments using reciprocation of cleaning/treatment fluid, a program executes the reciprocation cycle, i.e. to cause fluid to be reciprocated about the teeth, thereby providing the beneficial effect to the oral cavity, e.g. cleaning the teeth. Finally, system 10 has a program to empty mouthpiece 16 at the end of the reciprocation cycle, and a self-cleaning cycle to clean the system between uses, or at pre-set or automatic cleaning times.

Though not shown, a face panel with indicator lights may also be incorporated into system 10. Indicator, or display, lights include, but are not limited to, power on, charging, reciprocation program running, system emptying, cleaning results or feedback, and self-cleaning cycle in operation. In embodiments where fluid is pre-warmed prior to direction into application tray 16, a display light could be used to indicate that the liquid is at the proper temperature for use.

One method of using system 10 to collect saliva and clean/treat teeth is as follows. In the first step, the user positions application tray 16 in the oral cavity about the teeth and gingival area. The user closes down on tray 16, thereby achieving an effective fit or seal between gums, teeth and tray 16. In use of the system according to the invention, the user bites down on the mouthpiece, activating the switch in the mouthpiece to initiate the system. The full process is as follows:

1. System 10 is activated when the user bites down on mouthpiece 16, activating switch 20 to initiate the collection of saliva from the oral cavity. Flow valve 24 is closed, while flow valve 22 is opened. Pump 18 begins drawing saliva collected in application tray 16 through tube 33, pump 18, and flow valve 22, with the saliva collecting in saliva collection reservoir 12.

2. Once saliva collection is completed, system 10 is activated to begin dispensing cleaning/treatment fluid to application tray 16. Flow valve 22 is closed, while flow valve 24 is opened. Pump 18 begins drawing cleaning/treatment fluid from fluid supply reservoir 14 via tube 35, through flow valve 24, tube 33, and pump 18. Cleaning/treatment fluid is dispensed into application tray 16.

3. Cleaning/treatment continues until the time required has expired.

In an alternative method of using system 10 to collect saliva and clean/treat teeth, where the cleaning/treatment fluid is reciprocated through system 10, the user positions application tray 16 in the oral cavity about the teeth and gingival area. The user closes down on tray 16, thereby achieving an effective fit or seal between gums, teeth and tray 16. The user bites down on the mouthpiece, activating the switch in the mouthpiece to initiate the system. The full process is as follows:

1. System 10 is activated when the user bites down on mouthpiece 16, activating switch 20 to initiate the collection of saliva from the oral cavity. Flow valve 24 is closed, while flow valve 22 is opened. Pump 18 begins drawing saliva collected in application tray 16 through tube 33, pump 18, and flow valve 22, with the saliva collecting in saliva collection reservoir 12.

2. Once saliva collection is completed, system 10 is activated to begin dispensing cleaning/treatment fluid to application tray 16. Flow valve 22 is closed, while flow valve 24 is opened. Pump 18 begins drawing cleaning/treatment fluid from fluid supply reservoir 14 via tube 35, through flow valve 24, tube 33, and pump 18. Cleaning/treatment fluid is dispensed into application tray 16. Cleaning/treatment fluid is then drawn from application tray 16, through tube 31, and collected in fluid supply reservoir 14.

3. To reciprocate the cleaning fluid, the direction of the fluid flow is reversed by reversing the flow direction in pump 18. Flow valve 22 remains closed, while flow valve 24 remains opened. Pump 18 begins pumping cleaning/treatment fluid from application tray 16 via tube 33, through pump 18, tube 35, and flow valve 24, and into fluid supply reservoir 14. Cleaning/treatment fluid is then drawn through tube 31 and dispensed into application tray 16 by pump 18, thus completing one reciprocation cycle.

4. Steps 2 and 3 are repeated (reversing the flow direction) for each reciprocation cycle.

5. Step 4 is repeated until the time required for cleaning/treatment has expired, or the desired numbers of reciprocation cycles are complete.

It is noted that there may be a delay between steps 2 and 3 (in either or both, directions), allowing a dwell time where the fluid is allowed to contact the teeth without flow.

Figure 2:
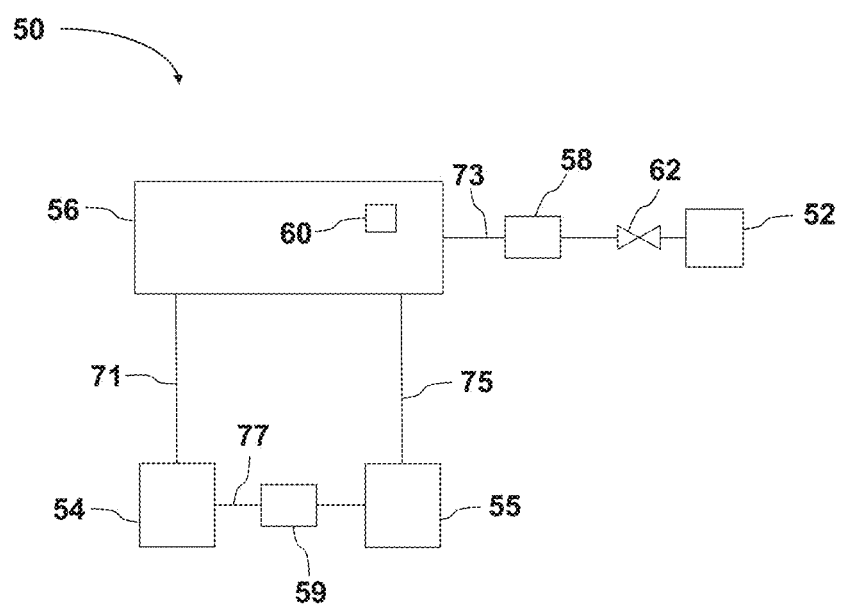
FIG. 2 is a schematic drawing of an alternative embodiment of an apparatus that may be utilized in the present invention.

FIG. 2 is a schematic drawing of an alternative embodiment of a system and method according to the present invention. The system designed to initially collect fresh saliva prior to the initiation of the cleaning/treatment process. The figure shows system 50, with components including: a saliva collection reservoir 52, fluid supply reservoirs 54 and 55, a means for directing the fluid onto the plurality of surfaces of the oral cavity, in this instance shown as application tray or mouthpiece 56, pumps 58 and 59, flow valve 62, and tubes 71, 73, 75, and 77 for conveying the fluid throughout the system. Switch 60 is disposed in or on mouthpiece 56 to initiate the saliva collection and cleaning/treatment cycle.

Pumps 58 and 59 may be piston pumps, valveless rotary piston pumps, diaphragm pumps, peristaltic pumps, gear pumps, rotary pumps, double-acting piston pumps, vane pumps, or similar. Fluid supply reservoirs 54 and 55 may be made of glass, plastic or metal. Fluid supply reservoirs 54 and 55 may be integral to system 50 and refillable. In some embodiments, fluid supply reservoirs 54 and 55 may be replaceable reservoirs 54 and 55 supplies, such as single or multi-use cartridges, detachably connected to system 50.

In some embodiments, fluid supply reservoirs 54 and 55 and/or tubes tubes 71, 73, 75, and 77 may include a heat source to pre-warm the fluid prior to direction into mouthpiece 56 for application to the surfaces of the oral cavity. The temperature should be maintained within a range effective to provide efficacy and comfort to the user during use.

Application tray 56, discussed in detail herein below, could be integral with, or detachably connected to system 50 by way of tubes 71, 73 and further attachment means (not shown). It could be one or two sided with internally, easily cleanable filters for trapping food particles. When positioned within the oral cavity, e.g. about the teeth and gums, mouthpiece 56 forms an effective fit or seal against the gums, and includes means to direct fluid against surfaces of the oral cavity, e.g. surfaces of the teeth.

During saliva collection, saliva collected in mouthpiece 56 flows through tube 73, pump 58, and flow valve 62 to saliva collection reservoir 52. During the cleaning/treatment cycle, fluid contained in the fluid supply reservoirs 54 and 55 flows through tubes 71 and 75 into mouthpiece 56. Pump 59 is used to pump the cleaning/treatment fluid to mouthpiece 56.

In this embodiment, during the cleaning/treatment cycle, fluid from mouthpiece 56 may return to fluid supply reservoirs 54 and 55 by flowing through tubes 71 and 75. This allows for small volumes of cleaning/treatment fluid to be used by system 50. Volumes of cleaning/treatment fluid used by system 50 can be less than about 40 ml, or less than about 30 ml, or less than about 20 ml, or less than about 10 ml.

In one embodiment, pump 59 draws fluid contained in fluid supply reservoir 54 through tube 77, pump 59, and into fluid supply reservoir 55. The liquid contained in fluid supply reservoir 55 is then forced through tube 75 and into mouthpiece 56. Fluid contained in mouthpiece 56 is forced through tube 71 and into fluid supply reservoir 54. The cleaning/treatment fluid continues to cycle through fluid supply reservoir 54, fluid supply reservoir 55 and mouthpiece 56.

In another embodiment, pump 59 draws fluid contained in fluid supply reservoir 55 through tube 77, pump 59, and into fluid supply reservoir 54. The fluid contained in fluid supply reservoir 54 is then forced through tube 1 and into mouthpiece 56. Fluid contained in mouthpiece 56 is forced through tube 75 and into fluid supply reservoir 55. The cleaning/treatment fluid continues to cycle through fluid supply reservoir 55, fluid supply reservoir 54 and mouthpiece 56.

In yet another embodiment, system 50 has means for providing reciprocation of fluid between fluid reservoirs 54 and 55 and mouthpiece 56. During the cleaning/treatment cycle, pump 59 may be first set to draw fluid contained in fluid supply reservoir 54 through tube 77, pump 59, and into fluid supply reservoir 55. The fluid contained in fluid supply reservoir 55 is then forced through tube 75 and into mouthpiece 56. Fluid contained in mouthpiece 56 is forced through tube 71 and into fluid supply reservoir 54. Then, the direction of flow is reversed, and pump 59 is set to draw fluid contained in fluid supply reservoir 55 through tube 77, pump 59, and into fluid supply reservoir 54. The fluid contained in fluid supply reservoir 54 is then forced through tube 71 and into mouthpiece 56. Fluid contained in mouthpiece 56 is forced through tube 75 and into fluid supply reservoir 55. In some embodiments, the direction of flow is reversed by reversing the flow direction of pump 59, such as with the use of a gear pump.

The saliva collection and cleaning/treatment actions of system 50 may be controlled by a logic circuit, which may include a program to start saliva collection when switch 60 is activated by a biting motion, and upon completion of saliva collection, the initiation of the cleaning/treatment cycle. In embodiments using reciprocation of cleaning/treatment fluid, a program executes the reciprocation cycle, i.e. to cause fluid to be reciprocated about the teeth, thereby providing the beneficial effect to the oral cavity, e.g. cleaning the teeth. Finally, system 50 has a program to empty mouthpiece 56 at the end of the reciprocation cycle, and a self-cleaning cycle to clean the system between uses, or at pre-set or automatic cleaning times.

As mentioned in the descriptions of the embodiments of FIG. 1, a face panel with indicator lights may also be incorporated into system 50. Indicator, or display, lights include, but are not limited to, power on, charging, reciprocation program running, system emptying, cleaning results or feedback, and self-cleaning cycle in operation. In embodiments where fluid is pre-warmed prior to direction into application tray 56, a display light could be used to indicate that the fluid is at the proper temperature for use.

One method of using system 50 to collect saliva and clean/treat teeth is as follows. In the first step, the user positions application tray 56 in the oral cavity about the teeth and gingival area. The user closes down on tray 56, thereby achieving an effective fit or seal between gums, teeth and tray 56. In use of the system according to the invention, the user bites down on the mouthpiece, activating the switch in the mouthpiece to initiate the system. The full process is as follows:

1. System 50 is activated when the user bites down on mouthpiece 56, activating switch 60 to initiate the collection of saliva from the oral cavity. Flow valve 62 is opened. Pump 58 begins drawing saliva collected in application tray 56 through tube 73, pump 58, and flow valve 62, with the saliva collecting in saliva collection reservoir 52.

2. Once saliva collection is completed, system 50 is activated to begin dispensing cleaning/treatment fluid to application tray 56. Flow valve 62 is closed. Pump 59 draws fluid contained in fluid supply reservoir 54 through tube 77, pump 59, and into fluid supply reservoir 55, forcing the fluid in supply reservoir 55 through tube 75 and into mouthpiece 56. Fluid contained in mouthpiece 56 is forced through tube 71 and into fluid supply reservoir 54.

3. Cleaning/treatment continues until the time required has expired.

Of course, if pump 59 is set to draw fluid from fluid supply reservoir 55, the steps described above are the same except for the direction of flow from fluid supply reservoirs 54 and 55 and mouthpiece 56.

In an alternative method of using system 50 to collect saliva and clean/treat teeth, where the cleaning/treatment fluid is reciprocated through system 50, the user positions application tray 56 in the oral cavity about the teeth and gingival area. The user closes down on tray 56, thereby achieving an effective fit or seal between gums, teeth and tray 56. The user bites down on the mouthpiece, activating the switch in the mouthpiece to initiate the system. The full process is as follows:

1. System 50 is activated when the user bites down on mouthpiece 56, activating switch 60 to initiate the collection of saliva from the oral cavity. Flow valve 62 is opened. Pump 58 begins drawing saliva collected in application tray 56 through tube 73, pump 58, and flow valve 62, with the saliva collecting in saliva collection reservoir 52.

2. Once saliva collection is completed, system 50 is activated to begin dispensing cleaning/treatment fluid to application tray 56. Flow valve 62 is closed. Pump 59 draws fluid contained in fluid supply reservoir 54 through tube 77, pump 59, and into fluid supply reservoir 55, forcing the fluid in supply reservoir 55 through tube 75 and into mouthpiece 56. Fluid contained in mouthpiece 56 is forced through tube 71 and into fluid supply reservoir 54.

3. To reciprocate the cleaning fluid, the direction of the fluid flow is reversed by reversing the flow direction in pump 59. Flow valve 22 remains closed. Pump 59 draws fluid contained in fluid supply reservoir 55 through tube 77, pump 59, and into fluid supply reservoir 54, forcing the fluid in supply reservoir 54 through tube 71 and into mouthpiece 56. Fluid contained in mouthpiece 56 is forced through tube 75 and into fluid supply reservoir 55, thus completing one reciprocation cycle.

4. Steps 2 and 3 are repeated (reversing the flow direction) for each reciprocation cycle.

5. Step 4 is repeated until the time required for cleaning/treatment has expired, or the desired numbers of reciprocation cycles are complete.

It is noted that there may be a delay between steps 2 and 3 (in either or both, directions), allowing a dwell time where the fluid is allowed to contact the teeth without flow.

Figure 3:
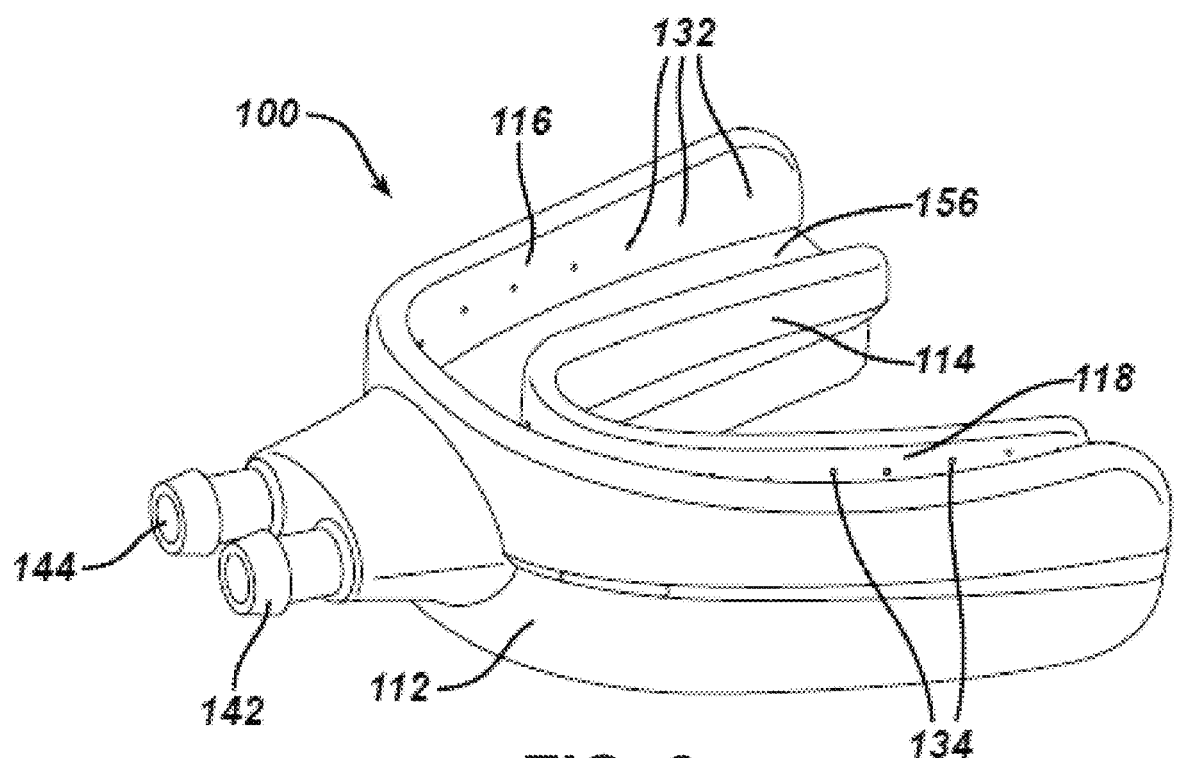
FIG. 3 is a top front perspective view of a first embodiment of an application tray that may be utilized in the present invention.
Figure 4:
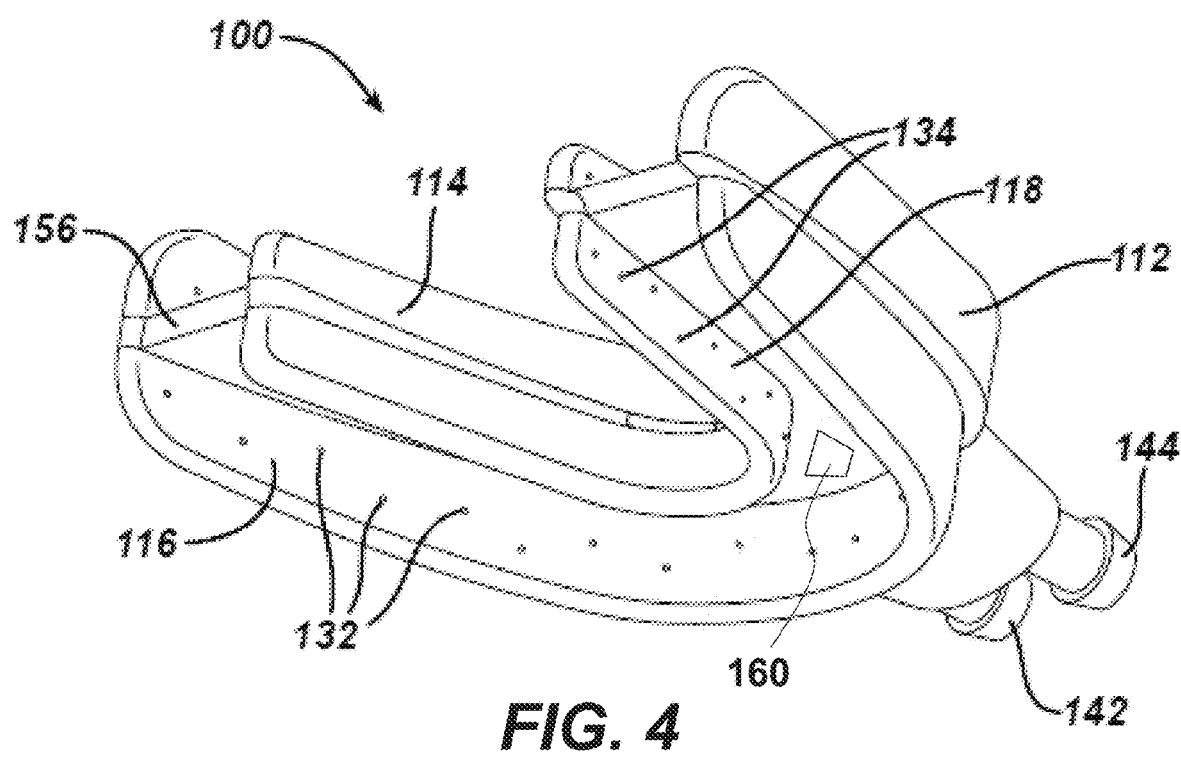
FIG. 4 is a bottom rear perspective view of the embodiment of the application tray of FIG. 3.

FIG. 3 is a top perspective view of a first embodiment of means for directing fluid, or liquid, onto a plurality of surfaces in the oral cavity, e.g. an application tray 100, according to the present invention. FIG. 4 is a bottom perspective view of the application tray 100 of FIG. 3. The figures show application tray 100 with outer front wall 112, outer back wall 114, inner front wall 116, inner back wall 118, and base membrane, e.g. bite plate, 156. Inner front wall jet slots 132 are located on inner front wall 116, while inner back wall jet slots 134 are located on inner back wall 118. The inner front wall jet slots 132 and inner back wall jet slots 134 shown in FIGS. 3 and 4 are only one embodiment of jet slot configuration. First port 142 and second port 144 enter application tray 100 through outer front wall 112.

FIGS. 3 and 4 depict an embodiment of an application tray 100 in which the user's top and bottom teeth and/or gingival area are substantially simultaneously contacted with liquid to provide the desired beneficial effect. It should be understood that in other embodiments, application tray 100 may be designed to clean and/or treat only the top or bottom teeth and/or gingival area of the user.

Figure 5:
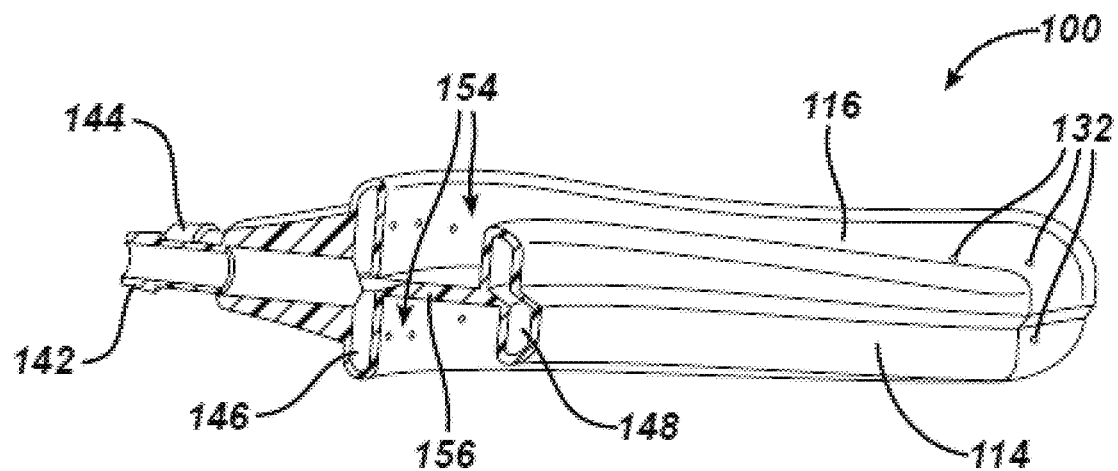
FIG. 5 is a vertical sectional view of the application tray of FIG. 3.
Figure 6:
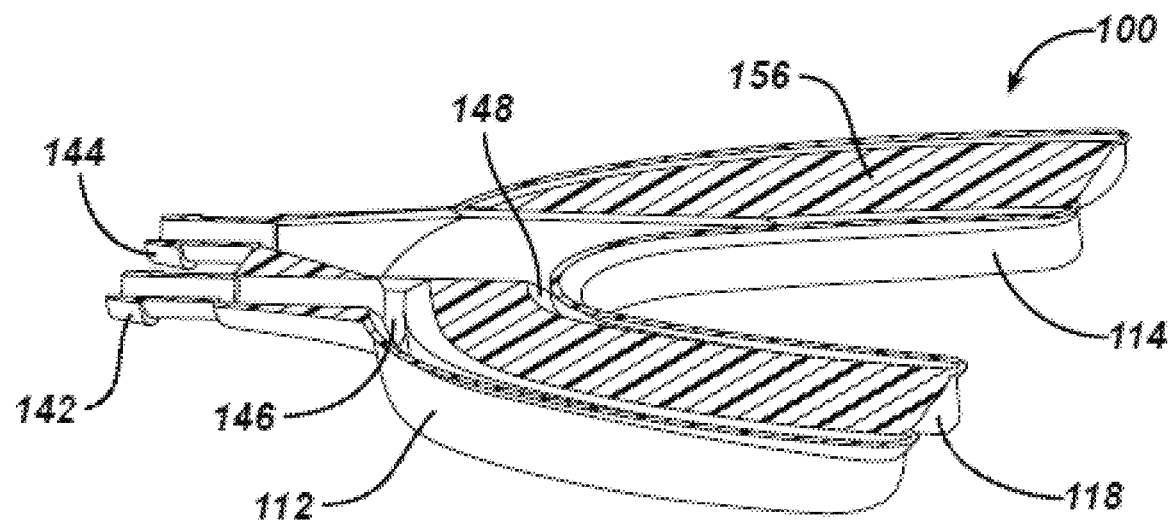
FIG. 6 is a horizontal sectional view of the application tray of FIG. 3.

FIGS. 5 and 6 are vertical and horizontal, respectively, sectional views of the application tray 100 of FIG. 3. The figures show first manifold 146, defined as the space bordered by outer front wall 112 and inner front wall 116. Second manifold 148 is defined as the space bordered by outer back wall 114 and inner back wall 118. The liquid-contacting chamber (LCC) 154 is defined by inner front wall 116, inner back wall 118, and base membrane 156.

In one embodiment of an operation, liquid enters first manifold 146 through first port 142 by pressure and then enters LCC 154 through inner front wall jet slots 132. A vacuum is pulled on second port 144 to pull the liquid through inner back wall jet slots 134, into second manifold 148 and finally into second port 144. In this embodiment, jets of liquid are first directed onto the front surfaces of the teeth and/or gingival area from one side of the LCC 154, directed through, between, and around the surfaces of the teeth and/or gingival area from the other side of LCC 154 into the second manifold to provide controlled interdental, gum line, surface and/or gingival area cleaning or treatment. Next, the flow in the manifolds is reversed. Cleaning liquid enters second manifold 148 through second port 144 by pressure and then enters LCC 154 through inner back wall jet slots 134. A vacuum is pulled on first port 142 to pull the liquid through inner front wall jet slots 132, into first manifold 146 and finally into first port 142. In the second portion of this embodiment, jets of liquid are directed onto the back surfaces of the teeth and/or gingival area, and directed through, between, and around the surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment it may be preferable to deliver the liquid through one or both manifolds simultaneously, flooding LCC 154, submerging the teeth for a period of time and then evacuating the LCC 154 after a set period of time through one or both manifolds. Here, cleaning or treating liquid simultaneously enters first manifold 146 through first port 142, and second manifold 148 through second port 144 by pressure and then enters LCC 154 simultaneously through inner front wall jet slots 132 and inner back wall jet slots 134. To evacuate LCC 154, a vacuum is simultaneously pulled on first manifold 146 through first port 142, and second manifold 148 through second port 144. Cleaning or treatment liquid is pulled through inner front wall jet slots 132 and inner back wall jet slots 134, into first manifold 146 and second manifold 148.

It is also possible to deliver different liquid compositions to first manifold 146 and second manifold 148. The different liquid compositions could then combine in the LCC for improved cleaning efficacy or treatment effects.

Gingival Seal

The gingival seal forms the bottom portion of the LCCM and contacts with the gingival tissue in such a way as to clean the gingival area, including the sub-gingival pocket. In one embodiment, it provides positioning of the mouthpiece relative to the oral cavity and teeth, and creates a relatively isolated environment with minimal/acceptable leakage during operation, while designed to minimize the gag factor and comfort for the user. In one embodiment, the gingival seal is created by the frictional engagement and compression of an elastomeric material with the gingival. This seal is enhanced during the evacuation of the liquid within and during the cleaning and treatment cycles. The seal also functions as a secondary mechanism for attaching and assembling the manifold and LCCM. The size and shape of the gingival or gum seal preferably utilizes three basic sizes (small, medium and large), but is designed to allow different levels of customization as required by the user for comfort and cleaning/treatment efficacy. These sizes are paired with the three basic sizes of the manifold and LCCM components.

Alternate embodiments for obtaining the gingival seal include the following and may be used in combination with each other or with the embodiment above:

Embodiment #1

The mouthpiece is positioned within the oral cavity and onto the gingival. The seal and position is fixed relative to the teeth and gingival when slight biting pressure is applied against the bite standoffs/locating blocks. The mouthpiece would be made out of a single or combination of materials of different hardness and resilience. In the preferred embodiment, the "H" shaped mouthpiece would have flexible walls (vertical edges of the "H") which would have a soft, resilient gasket-like material (closed cell silicone, gel filled seal, etc.) at the ends of each of the "H" legs. The horizontal pad of the "H" would include biting blocks/standoffs for positioning the mouthpiece in the X, Y, and/or Z locations, relative to the teeth and gingival. Once the mouthpiece is positioned in the oral cavity, closing of the upper and lower jaw to engage the bite blocks would provide positive and rigid positioning of the mouthpiece relative to the oral cavity, while providing interference of the gasket-like material with the gingival material to provide an effective seal and formation of the cleaning, treatment, and/or diagnostic cavity for the duration of the operation.

Embodiment #2

Force applied to the mouthpiece to create inward movement of sidewalls, sealing a soft resilient edge against the gingival tissue. A mouthpiece similar to that described in embodiment #1 would also provide an active locking feature to improve the engagement of the seal. One potential execution of this would require that a hollow section be designed within the horizontal leg and between some or all of the standoffs between the upper and lower sections of the mouthpiece, when the device is not engaged. After the mouthpiece is placed in the oral cavity, the user bites down and compresses the hollow section, which then collapses so that all the bite blocks are in contact. This in turn causes the external walls (the vertical leg portions) to fold inwardly towards the gingival tissue. The resilient gasket attached to these walls engages and compresses against the gingival to create the seal and the cleaning, diagnostic, and/or treatment chamber surrounding the upper and lower teeth.

Embodiment #3

A pneumatic bladder is inflated or pressurized when the mouthpiece is positioned in the oral cavity to create the seal and cavity with the gingival. A mouthpiece similar to that described in embodiment #1 could also provide an active seal through the inflation of a bladder, or bladders, within the mouthpiece. The air could also subsequently be utilized to clean and or dry the teeth/cavity and/or provide treatment (gas and or entrained particle in gas) for treatment, cleaning and/or diagnostics.

Embodiment #4

A hydraulic bladder is inflated or pressurized when the mouthpiece is positioned in the oral cavity to create the seal and cavity with the gingival. A mouthpiece similar to that described in embodiment #1 could also provide an active seal through the pressurization of a bladder(s) within the mouthpiece. The liquid composition could also subsequently be utilized to clean and/or treat the teeth and or gingival tissue with or without gas or entrained particles for cleaning, treatment, or diagnostics.

Embodiment #5

After the mouthpiece is positioned in the oral cavity, the seal is created through a change in compliance of the material engaging the gingival with or without expansion of the material to seal around the gingival due to liquid absorption (utilize a hydrogel, etc.).

Embodiment #6

After the mouthpiece is positioned in the oral cavity, Nitanol wire or other shape-memory materials embedded into the mouthpiece cause the side walls to engage the gingival due to the change of body temperature in the oral cavity, creating a positive seal with the gingival tissue.

Embodiment #10

A foam-like material is extruded into the mouthpiece area initially or alternatively during each use to create the mouthpiece seal and subsequent cleaning, treatment, and diagnostic cavity.

Embodiment #11

A disposable or dissolvable insert is provided to provide the seal to the gingival tissue for multiple or each use of the mouthpiece.

Embodiment #12

An adhesive is contained on the gum seal contact surface, which can be saliva or water activated. Adhesive would provide potential seal improvement and could be single use or multiple use application, depending on the formulation. Sealing system can be used with any combination of other sealing systems discussed.

Embodiment #13

The gingival seal is created through a combination of material on contact area and geometry at the interface that creates a suction-like effect in the seal contact area (suction cup) through creation of a vacuum in this area during the engagement.

Embodiment #14

The gingival seal area can be made and customized to a user's mouth by utilizing a deformable material that can be placed and positioned against the gingival, which then takes on a permanent set for the user. This may be created through boiling and placing in the mouth and pressing against the gingival by closing the jaw and or like method, then removing from the oral cavity (similar to a mouth guard). As the sealing material cools, it takes on a permanent set.

Embodiment #15

The gingival seal area can be created by taking a generic or semi generic bladder and placing into the oral cavity in close proximity to the desired gingival seal contact area. This bladder can then be filled and directionally supported to engage and conform against the gingival. The filling material would be a fast curing material, which would take set to provide the customized sealing form, which would then be reusable by this specific user. The bladder could be a TPE and/or thin silicone-based material, and the filling material could be an RTV, epoxy, polyurethane or similar material to provide a rigid, semi rigid or flexible permanent set form when cured or set.

In a preferred embodiment, the gingival effective seal is a contact seal created by the geometry of the LCCM bottom edge engaging the gingiva. The LCCM bottom edge is preferably flexible to allow conformance to different user's gingival surfaces below the gum line and along the points of contact. This portion also needs to be soft enough so as not to cause abrasion or damage to the gingival region to provide comfort to the user, while maintaining an effective seal. In the preferred geometry, the LCCM contact area provides a radial and or curved smooth surface to provide point of contact and a comfortable sealing. The preferred material of this edge would be a low durometer silicone, under 100 Ra, and more preferably between 15 Ra and 70 Ra, due to its durability and inherent performance characteristics, but could also be soft and/or flexible materials, such as TPE's and other materials know in the art.

The effective seal is formed in conjunction with the operation of the vacuum and removal of saliva from the LCC, allowing any residual leakage from the universal appliance to be pulled back into the LCC and the hand-held device for subsequent removal.

Components

The entire system will be modular in nature so individual components can be easily replaced by the user. Reasons for replacement include but are not limited to wear, malfunction, and biohazard. Some components may also be disposable and replaceable by nature (refill cartridges, etc), thus modular and easily replaced by the user.

Pump System

In one embodiment, the liquid may be delivered from a reservoir in the mouthpiece handle or base station via a powered pump. The pump may be capable of responding to input from a logic system (artificial intelligence, or AI) to vary pressure, cycle time (for each stage and total process), reciprocating motion requirement and/or timing, direction of flow, liquid velocity/pressure, purge specifications, and similar. The pumps may be s-piston pumps, valveless rotary piston pumps, diaphragm pumps, peristaltic pumps, gear pumps, rotary pumps, double-acting piston pumps, vane pumps, or similar. A charged pneumatic cylinder or air compressor may also drive the system as an alternative embodiment. The cycle time for the total process, cycle time for each individual stage, and flow velocity for each stage of the cycle may be variable and potentially customized to each individual user/day of the week/oral health conditions. It is also possible to change the volume of liquid delivered per stroke or over a time period in different offerings of the system, depending on the needs of the specific user and specific treatment requirements. The pump system may be in the hand piece or in the base station. The volume of liquid may be relatively large to give the effect of pulses of liquid in the mouthpiece. An alternatively embodiment has a pump that delivers constant flow with low or no pulsations. The direction of the liquid to and from the mouthpiece can be reversed by changing the direction of the motor in a rotary valveless pump, gear pump, or other means. The liquid drive system will not start until the mouthpiece is properly inserted and sealed against the gums. The system will automatically stop dispensing and may remove residual liquid from the mouth once the mouthpiece is removed (effective seal against gums is broken) from the mouth. This will allow the user to safely increase the concentrations of active ingredients in the cleaning/treatment formulation. The system will not start until the mouthpiece has an effective seal against the gums. In one embodiment the pump system is entirely contained in the hand piece, and in another the pump system is housed in the base station.

Valving/Liquid Control & Liquid Input/Output

It may be desirable to change the direction of the flow to the mouthpiece if the mouthpiece embodiment is used wherein the mouthpiece has one inlet and one outlet. The direction of liquid flow through the teeth would be reversed by changing the direction of flow of the inlet and outlet to the mouthpiece, therefore increasing the efficacy and sensory effects of the cleaning process. The mouthpiece may have nozzles on opposite sides of the teeth wherein one side of the jets are pressured and the opposite side draws a negative pressure differential. This forces the liquid "through/between" the teeth. The flow is then reversed on each set of nozzles to move the liquid the opposite direction through the teeth. The liquid may then be reciprocated back and forth. The direction of flow may be reversed and/or reciprocated by reversing the direction of a specialized pump, such as a gear pump or rotary valveless pump. Another embodiment includes but is not limited to reversible check valves, wherein the orientation of the check valves to the pump is reversed, thereby reversing the direction of the flow throughout the system. Another embodiment includes two controlling 3-way valves with the logic (AI) system to reverse the direction of flow when activated. A further embodiment has a logic (AI) system to one controlling 4-way valve with one input from the pump, a return to the pump, and two outlets to the mouthpiece that can reverse flow direction as desired. Another embodiment involves configuring tubing so as to shut off of the flow with pinch valves to specific tubes in order to reverse the flow of the system. Another embodiment includes development of a liquid control switching box that connects two tubes on one side of the box to two tubes on the opposite side of the box. In one orientation the liquid flow moves directly across the box from one collinear tube to the next, while in the other position the liquid flow moves in an "X" direction whereby liquid flow direction is "crossed" in the switching box. In another embodiment, flow is reciprocated by using a double-acting piston pump, wherein the flow is constantly reciprocated back & forth between the two piston pump heads.

In one embodiment the liquid control system is entirely contained in the hand piece, and in another embodiment, the liquid control system is housed in the base station. The tubing used in the system must withstand both pressure and vacuum states.

One or more liquid types from individual reservoirs can be delivered through the mouthpiece individually or combined. Any combination and concentration variation can be used. The reservoirs may reside in the hand piece or in the base station.

The system may include manual and/or automatic air purging, and/or an accumulator to provide system compressibility.

The valving system for directing and controlling fluid to and from the vacuum and delivery pumping systems may be optimized to provide a modular, cost effective, efficient system that allows for simplified manufacturing and assembly. In addition, improved maintenance of the system can be achieved by using a cut sheet of flexible film sandwiched between two injection moldable components.

The switching/fluid reciprocation control system to create the fluid reciprocation can be mechanical (driven via mechanism/gearing or electrical (electrically controlled valving such as multi-way solenoid flow valves, initiated via an electrical signal). In the preferred mechanical embodiment, the switching system is driven off the pump drive motor(s), so as to minimize the size, complexity and cost of the overall system. This is completed via mechanical linkages and gearing as shown below, driving the unique switching mechanism. The switching mechanism can be reciprocative in nature, such as a cam engaging a slide switching member, pushing it back and forth. It can also be a unique, continuous revolving switching disk member as shown in the exploded and cross-sectional views below, switching fluid direction 2 times for every single rotation of the disk, due to the unique D-shaped flow channel. The design provides a built-in pressure relief valve like function that allows flow crossover when switching flow directions, without any additional hardware, to minimize strain on the drive motor/system and increasing life of the motor/system.

Interface (Electrical & Liquid)

The hand piece may have an electrical and/or communication system that interfaces with the base station. This includes but is not limited to charging of the rechargeable battery, transferring diagnostic information between the units, transferring custom profile information between the units, and transferring program-related information between the units. Information can be transferred wirelessly (RFID, 802.11, infrared, etc.) or through a hard connection. The electrical system will include logic so as to control the function, start, and stop of the system based on preset criteria. The criteria may include starting only after a seal has been created between the mouthpiece and the gums, ensuring a properly charged liquid system, ensuring a minimum battery charge level, ensuring the liquid level is within a specified range, etc. There may be a logic system that may communicate with various components of the device including, but not limited to, initiating algorithms to control the sequencing of the valves, motion of the piston and therefore motion of the liquid, receive inputs from the consumer, receive inputs from the temperature sensor, receive diagnostic input, detect engagement of the mouthpiece seal against the gums, etc. The logic system must be capable of processing and responding to an input and outputting appropriate data. The system may include redundant circuitry wherein providing a fail-safe design.

The system may include a means to provide feedback to the user such as lights, display, touch screen, recorded messages, vibration, sounds, smell, and similar. It may also have a means to operate the system and select processes/settings, such as switches, touch screens, buttons, voice commands, and similar.

The system may include a means for tracking statistics such as time between uses, length of use/cycle, total uses, regimen details (amount and time of each liquid/treatment), time to replace specific system components, and similar. The system may provide feedback to the user to indicate time to replace or refill, wear, disposable, or replaceable components.

There will be a method of liquid supply, which may be a liquid reservoir, hose supply system, or similar. The liquid supply may be located in the base station and transferred to a reservoir in the hand piece when the hand piece is docked in the base station. The liquid may then be delivered through the mouthpiece during the cleaning process, and purged out of the system delivery and/or after the cleaning process. In another embodiment, the hand piece is connected to the base station with a liquid connection means, and liquid is delivered from a reservoir in the base station, through the hand piece, directly to the mouthpiece.

There may be consumable cartridges that may contain treatment solutions, cleaning solutions, diagnostic solutions, or similar. The cartridges may be modular in design so as to be easily replaceable by the user.

The system may include a means of detecting the level of plaque on the teeth. One such method of detection is by coating the teeth with a fluorescein solution, which has been proven to stick to plaque, and monitoring the light waves emitted from the fluorescein-coated plaque vs. uncoated teeth regions. The light wave is different for each region, therefore it is discernable which areas and how much plaque exists on the teeth. Other similar methods of plaque detection may also be used, such as vision systems.

Cleaning/Purging/Charging

The liquid system may be charged with disposable cartridges, refilling of a chamber, accessing a main reservoir in the base station with tubing, or other means of liquid transfer (gravimetric, hand pump, siphon pump, use of main pump drive or secondary system to fill/charge reservoirs, and similar). The liquid reservoirs may be filled with a combination of different liquids to create a unique combination of different liquid concentrations. In another embodiment, ingredients may initially be in a form other than liquid (gel, powder, tablet, and similar) and may be combined with liquid for added treatment and/or cleaning benefits.

The hand piece will have a purge setting that is simply and easily activated by the user during and/or after the cleaning process. This can be accomplished with a method such as a single button pushed by the user that will purge the hand piece of liquid and waste. In another embodiment, the excess liquid and waste is transferred from the hand piece to a waste reservoir or the sink drain, outside of or docked in the base station. There may be a filtration system to protect the components from contaminants. In a further embodiment, the hand piece houses a disposable waste cartridge. In an alternate embodiment, the mouthpiece is cleaned in the base station between uses. The cleaning method includes, but is not limited to, UV cleaning, alcohol bath, alternate cleaning liquid bath, or other similar method. The liquid cleaning bath may or may not circulate in and/or around the mouthpiece.

Drive System

The liquid system may be driven by a rotary motor with means to translate motion from rotation to linear movement. This may be achieved via eccentric cam, linear sliders, or other known methods. In an alternate embodiment, a linear motor, or series of linear motors, may drive the system. This would possibly reduce the size of the liquid system and gain additional control of liquid delivery through liquid vacuum. The motor(s) may directly drive the pistons up and down in a translational fashion.

In order to optimize the design and minimize the size of the device, the components of the linear drive may be integrated into the pump system. The piston itself may incorporate the magnet and the coil may be imbedded in or around the outer piston chamber walls. Alternatively the piston and/or fixed attachment means to piston can be moving portion and the magnet can be stationary (i.e. surrounding or within the piston walls). In addition, both the vacuum and delivery pistons may have imbedded magnets that act against one another to create or assist with the piston movement.

The motor will also drive the movement of the reciprocating flow controller. A rotary motor may have a worm, bevel, or similar gear assembly to translate the motor rotation to spin the reciprocating flow controller. The outer circumference of the reciprocating flow controller may be comprised of gear teeth, which may be used as a means to rotate the reciprocating flow controller disk from the translated motor rotation. Alternatively, a linear motor may drive the FDM in a ratcheting fashion or geared fashion, such as motion transference like the geneva mechanism.

In some embodiments, the pumping and vacuum sections may be oriented in-line with one another. Alternatively, they may be oriented parallel to each other. Each orientation has different advantages in regard to compactness. The pumping and vacuum sections can be connected together, or alternatively operate independently, being synchronized in frequency and/or some factor of frequency (i.e. vacuum section could have the volumetric displacement of the delivery section, but move at a different speed) or could run asynchronously. If the delivery and vacuum sections are oriented in-line with one another, they may be connected to each other via a rod. This may allow the delivery and vacuum pistons to be driven simultaneously, ensuring synchronization between the pumping and vacuum strokes.

The delivery piston may be driven by the same rod that drives the vacuum piston, but may have also some damping means and or delay one to the other, such as slot where it attaches to the piston. This may allow for extra play in the drive piston, causing the vacuum stroke to start slightly before the delivery stroke and continue slightly after the delivery stroke. This may give the vacuum stroke additional opportunity to remove liquid from the appliance since it is still creating a vacuum while the delivery piston is dwelling, as well as minimizing leakage due to gravity and appliance position into the oral cavity.

The vacuum piston and delivery piston may have means to dump liquid into reservoir as a safety, in case either experiences any sort of partial or full blockage, which could result in premature failure of device components (motors, valves, seals, etc). This allows for safe and controlled operation and prevents over pressurization when the main flow ports are have been compromised and repeatable device performance for efficacy. By dumping into the local reservoir instead of to atmosphere, leakage potential outside of the device is minimized.

Temperature Control

In one embodiment, the liquid temperature may be controlled within a specified range. If the liquid is too cold, it may cause discomfort and sensitivity in the user's mouth. If the liquid temperature is too high, it may cause discomfort, sensitivity, and damage to the user's mouth. The system may be confirmed not to run if the liquid temperature above the specified limit. A heating element may increase the temperature if it is below the minimum specified limit. The system may be confirmed not to run unless the liquid temperature is within the specified range. The temperature feedback may be provided, but is not limited to thermistors, thermocouples, IR or other temperature monitoring means. This information may be fed back to the logic (AI) system.

The drive system may have means to heat the liquid to a specific temperature range. Liquid may be heated in one or more locations of the system. Methods of heating the liquid include, but are not limited to, an inductive element, a radiant element, a ceramic element, a tubular sealed heating element (e.g. a fine coil of Nickel chrome wire in an insulating binder (MgO, alumina powder), sealed inside a tube made of stainless steel or brass), a silicone heater, a mica heater, or an infrared heater.

FIGS. 7a-7l show an example of an embodiment of a dental cleaning system 2000 of the present invention. The figures show dental cleaning system 2000, showing hand piece 2220, base station 2250, and base station liquid reservoir 2280. Base station liquid reservoir 2280 is used to refill the liquid reservoirs in hand piece 2220. Application tray 2100 is shown attached to hand piece 2220.

In this embodiment, base station filling tube 2245 is the conduit through which cleaning or treatment liquid passes from base station liquid reservoir 2280 to the liquid reservoirs in hand piece 2220. Liquid leaves base station liquid reservoir 2280 through base station liquid reservoir port 2285, and enters the liquid reservoirs in hand piece 2220 through hand piece port 2225.

When in base station 2250, the internal battery of hand piece 2220 will recharge, and the liquid reservoirs in hand piece 2220 will refill from those in base station 2250. Any diagnostic information in hand piece 2220 will be exchanged with base station 2250. Hand piece 2220 may also go through a cleaning process.

Figure 7A:
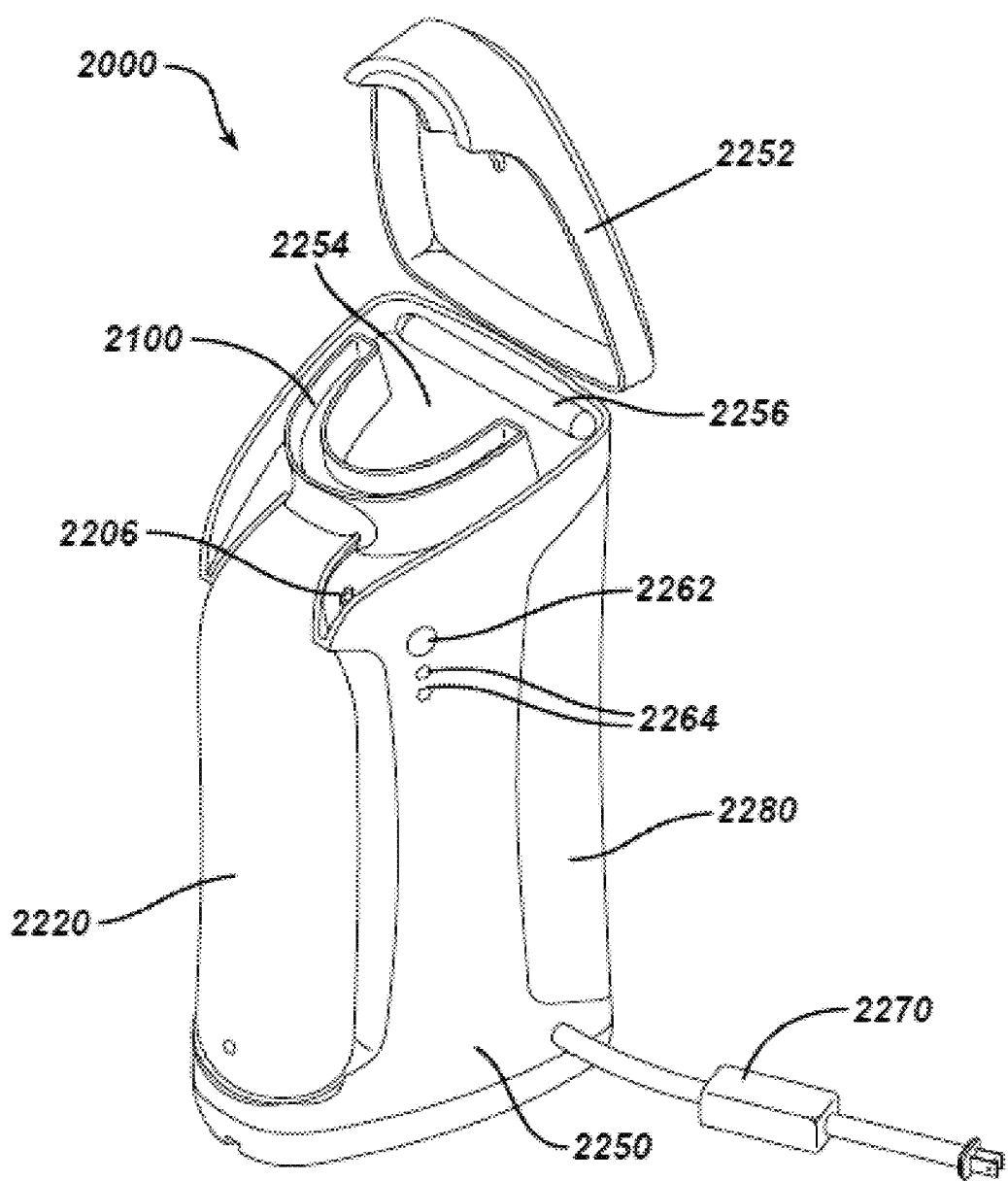
FIG. 7a is a front, top perspective view of an embodiment of a system that may be utilized in the present invention.

FIG. 7a is a front, top perspective view of an embodiment of a dental cleaning system 2000, including hand piece 2220, base station 2250, and base station liquid reservoir 2280. Base station 2250 includes base station lid 2252, sanitation chamber 2254, UV sanitizing light 2256, UV light kill switch 2206, start button 2262, indicator lights 2264, and power cord with AC adapter 2270. UV sanitizing light 2256 in sanitation chamber 2254, is used to sanitize application tray 2100 between uses. UV light kill switch 2206 shuts down UV sanitizing light 2256 when base station lid 2252 is opened or ajar. The UV kill switch can also be utilized to initiate the sanitation process when the lid is closed, and the hand piece is docked. Indicator lights 2264 can be used to inform the user of the status of hand piece 2220 charge, position, or sanitation status, or the status of the base station liquid reservoir 2280 (full/empty, for example).

Figure 7B:
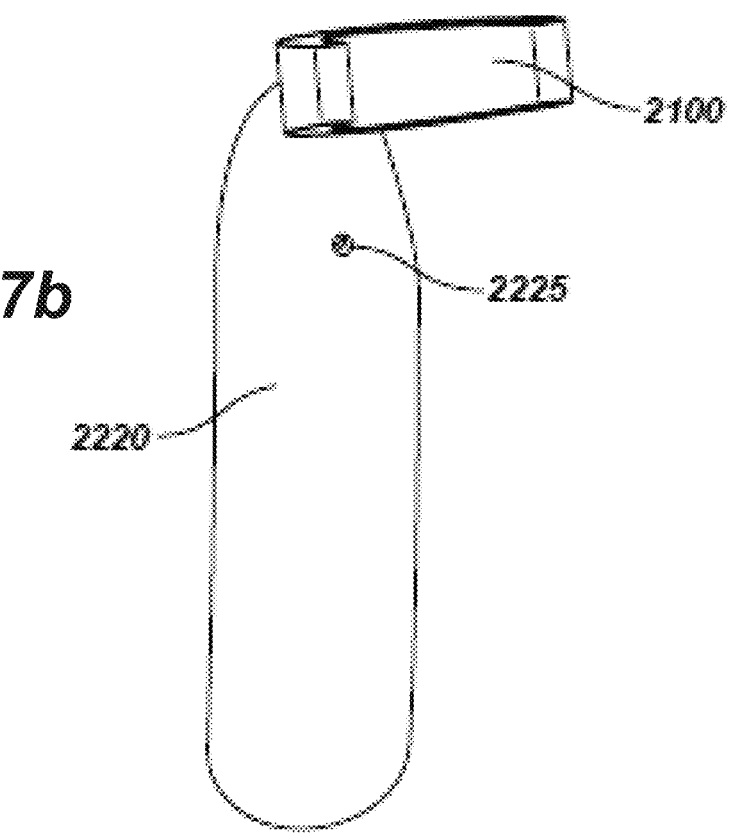
FIG. 7b is a front, top perspective view of the hand piece section of the system.

Hand piece 2220 includes attached application tray 2100, and as shown in FIG. 7b, and hand piece port 2225. Fluid enters and exits hand piece 2220 through hand piece port 2225.

Figure 7C:
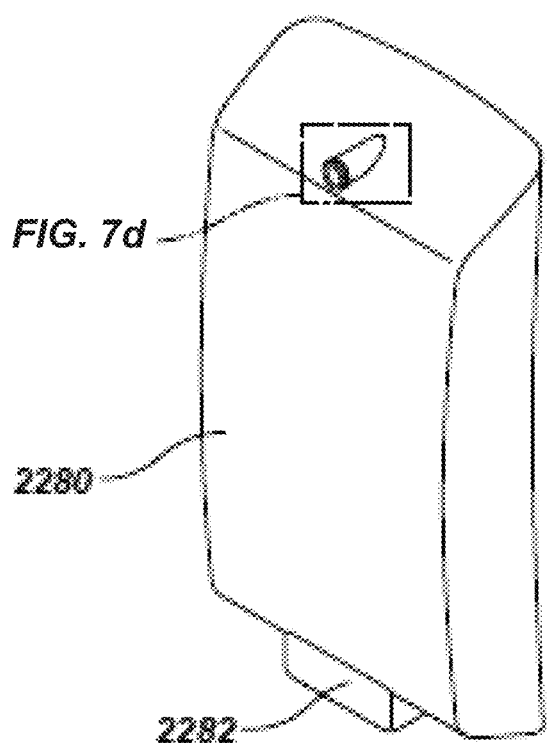
FIG. 7c is a front, top perspective view of the fluid reservoir section of the system.
Figure 7D:
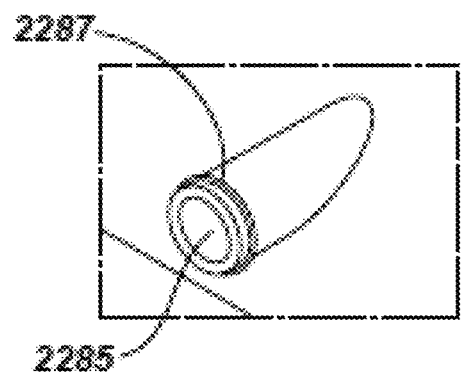
FIG. 7d is an inset view of a region of the fluid reservoir of FIG. 7c.

A front, top perspective view of base station liquid reservoir 2280 is shown in FIG. 7c. As shown in the inset view of base station liquid reservoir 2280 (FIG. 7d), base station liquid reservoir 2280 includes base station liquid reservoir port 2285, from which fresh fluid is used to fill hand piece 2220, and base station liquid reservoir locking feature 2282, used to engage base station liquid reservoir 2280 to base station 2250. Base station liquid reservoir port 2285 includes O-ring 2287 to insure a seal between reservoir port 2285 and base station inlet tube 2245a.

Figure 7E:
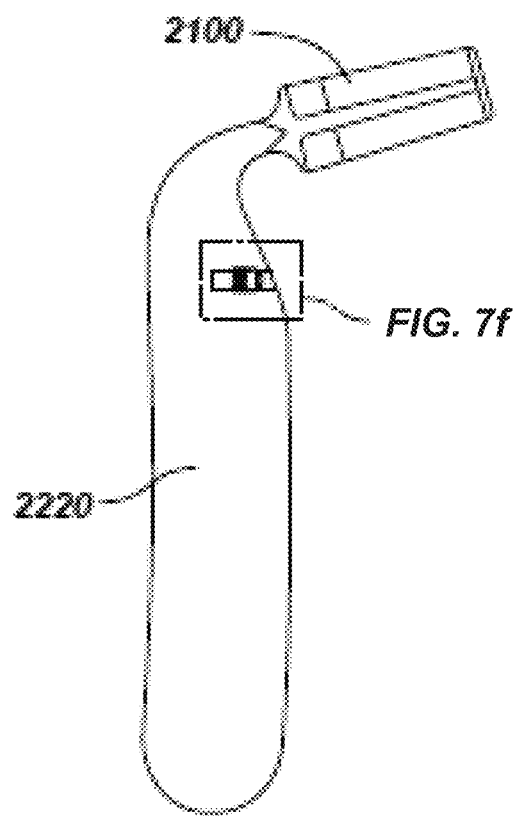
FIG. 7e is cross-sectional view of the hand piece section of the system.
Figure 7F:
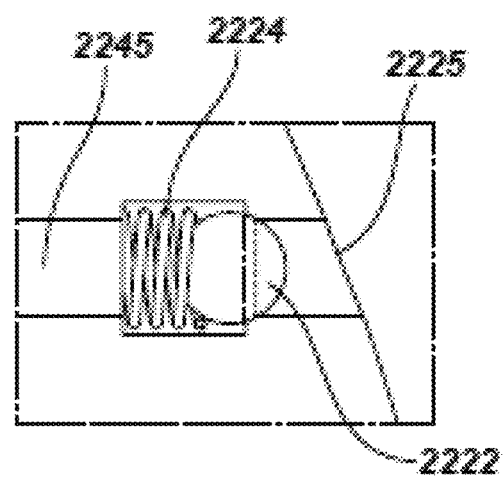
FIG. 7f is an inset view of a region of the hand piece of FIG. 7e.

A partial cross-section of hand piece 2220 is shown in FIG. 7e. As shown in the inset view of hand piece 2220 (FIG. 7f, hand piece port 2225 includes hand piece port 2225, from which fresh fluid is used to fill hand piece 2220. Hand piece port 2225 includes ball bearing 2222 and spring 2224 assembly. Fluid entering hand piece 2220 through hand piece port 2225 passes through ball bearing 2222 and spring 2224 assembly, which act as a sealing means for hand piece 2220, when not engaged in the base station.

Figure 7H:
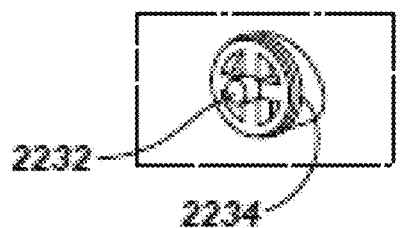
FIG. 7h is an inset view of a region of base station of FIG. 7g.
Figure 7G:
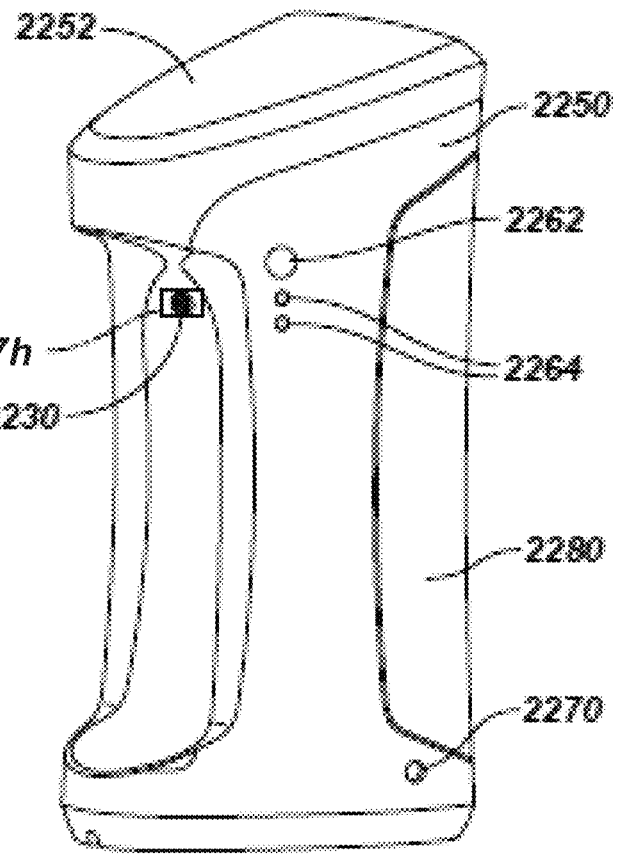
FIG. 7g is a front, top perspective view of the system of FIG. 7a, with the fluid reservoir attached to the base station.

FIG. 7g with inset view FIG. 7h shows the base station-to-hand piece docking feature 2232. Fluid from base station port 2230 passes through docking feature 2232 prior to entering hand piece port 2225. O-ring 2234 insures a seal between base station port 2230 and hand piece port 2225. A switch/sensor may also be located in the base station 2250 hand piece docking area to ensure hand piece 2220 is in the proper docking position for fluid loading from base station 2250 and/or initiation of the appliance tray sanitation process. The hand-held position/docking status may also be verified through feedback of the base station to hand held charging circuit.

Figure 7I:
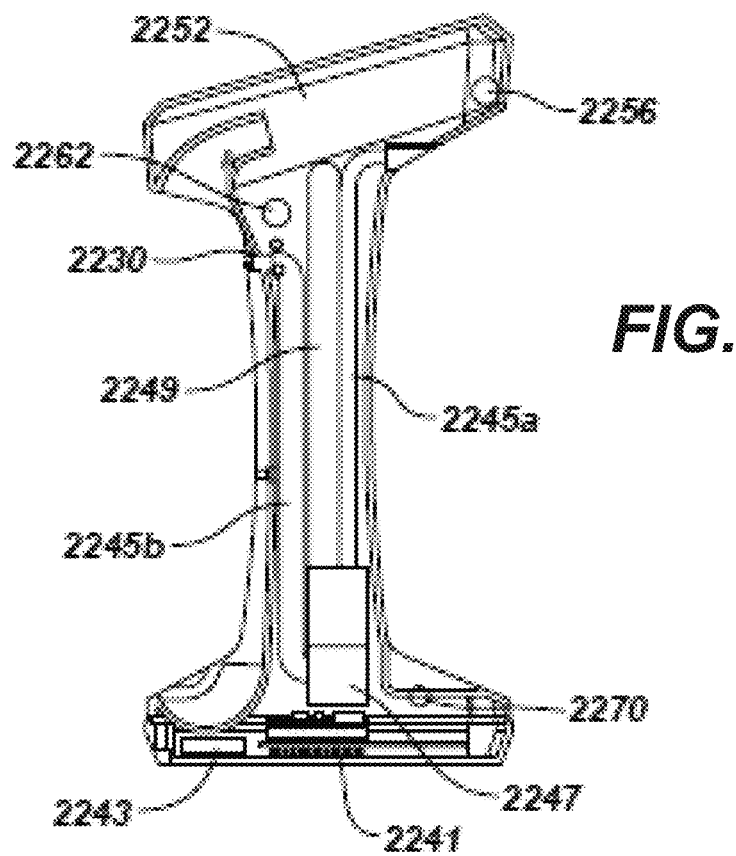

FIG. 7i is a cut-away view of base station 2250 without hand piece 2220 or base station liquid reservoir 2280 attached. The cut-away view shows pump 2247, heating coil 2249, reservoir to pump tube 2245a, base station pump to base station port tube 2245b, as well as the microcontroller and circuit board 2241 and hand piece charging pad 2243 located on base station 2250.

Figure 7J:
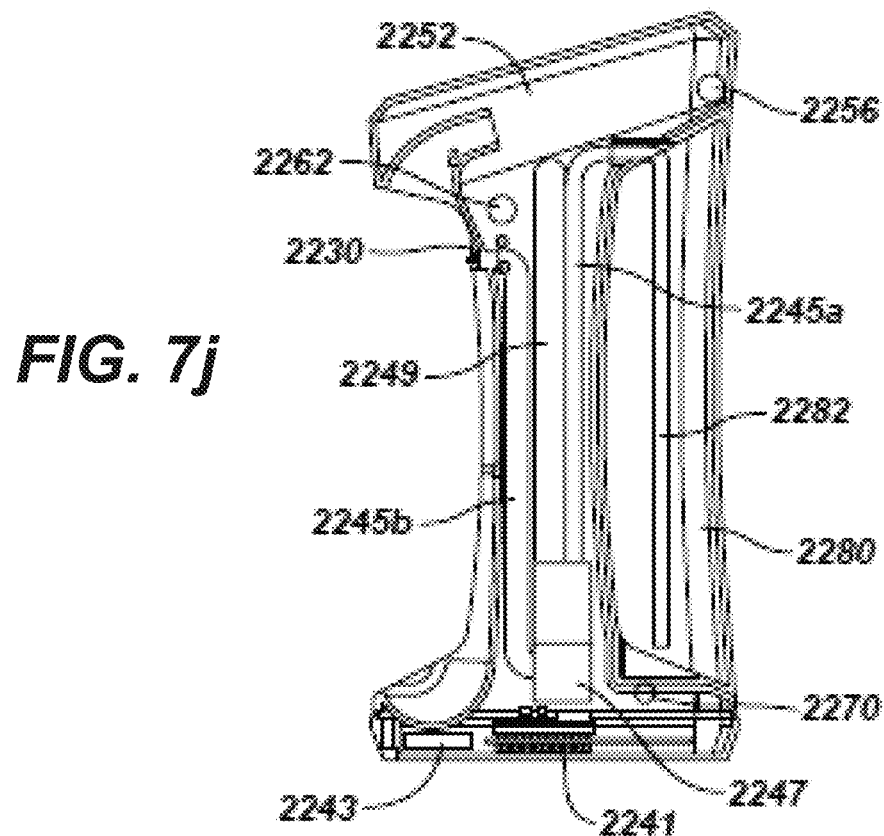
FIG. 7j is a cut-away view of the system of FIG. 7a, with the fluid reservoir attached to the base station.

FIG. 7j is a cut-away view base station 2250 with base station liquid reservoir 2280 attached. Base station liquid reservoir locking feature 2282 is used to engage base station liquid reservoir 2280 to base station 2250. When engaged, fluid in base station liquid reservoir 2280 can pass through base station reservoir tube 2282, exiting base station liquid reservoir 2280 through reservoir port 2285 and entering base station 2250 through base station inlet tube 2245a. Heating coil 2249 is used to warm fluids in tubes 2245a and 2245b prior to the fluid entering hand piece 2220.

Figure 7K:
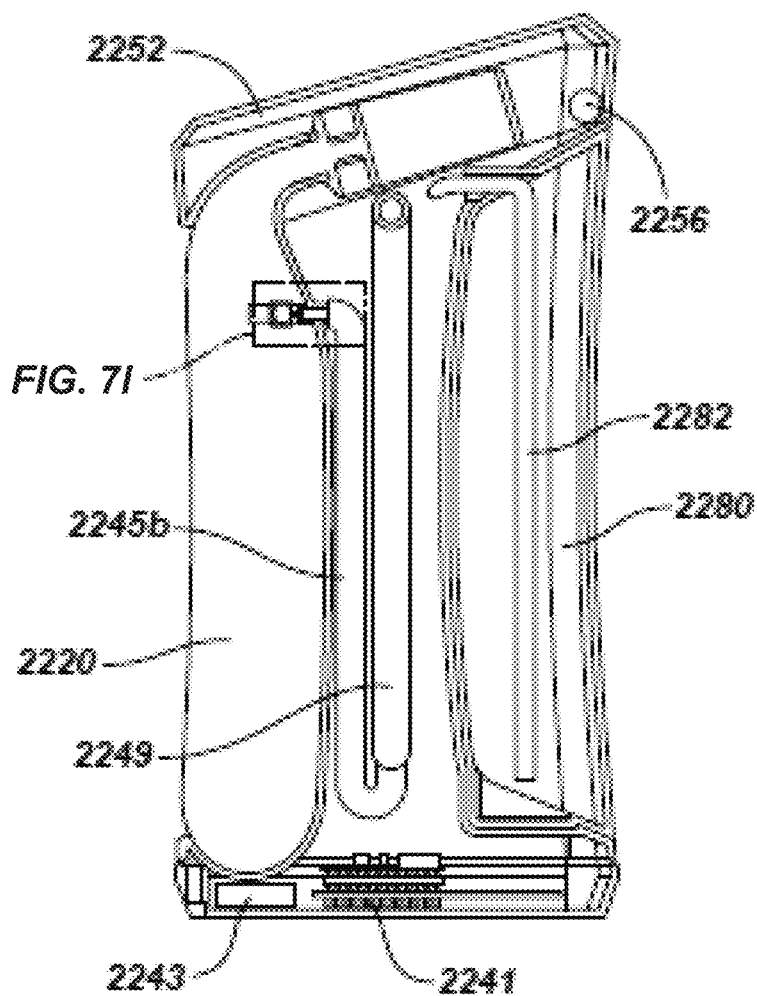
FIG. 7k is a cut-away view of the system of FIG. 7a, with the fluid reservoir and the hand piece attached to the base station.
Figure 7L:
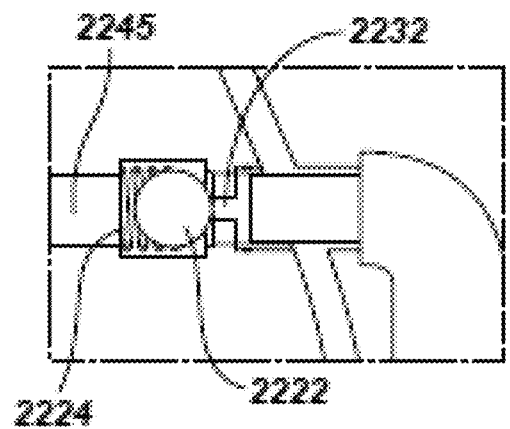
FIG. 7l is an inset view of a region of base station and hand piece of FIG. 7k.

FIG. 7k is a cut-away view of base station 2250 with hand piece 2220 and base station liquid reservoir 2280 attached. As shown in inset view (FIG. 7l), when hand piece 2220 is attached to base station 2250, docking feature 2232 contacts ball bearing 2222 and spring 2224 assembly, displacing ball bearing 2222 and allowing fluid to fill hand piece 2220.

In this embodiment, base station liquid reservoir 2280 would be loaded in base station 2250, containing sufficient fluid quantity to allow reservoir 2280 to be used a number of times before being empty. The removable and replaceable reservoir 2280 would engage with the base station 2250 through liquid reservoir locking feature 2282 to both correctly position and hold reservoir 2280 in base station 2250, and provide a seal for fluid conduit into the base station 2250.

Fluid would be pumped from base station liquid reservoir 2280 past heating coil 2249 where it would be heated to an acceptable temperature to minimize sensitivity when applied into the LCC when applied during the cleaning/treatment process.

Hand piece 2220 is placed into the handle dock in base station 2250 by the user. Hand piece 2220 engages with base station 2250 through docking features to both correctly position and hold hand piece 2220 in the correct position in base station 2250 to allow fluid to be pumped from base station liquid reservoir 2280 and into the local reservoir in hand piece 2220. Hand piece 2220 includes a feature that is opened to provide the conduit for fluid flow from base station 2250 when properly placed in the docking station. When hand piece 2220 is removed from base station 2250, the fluid channel is automatically closed and sealed.

In summary, base station 2250 houses the handle fluid loading system, the fluid heating system, the mouthpiece UV sanitation chamber, the handheld charging station, and control electronics and signal conditioning to control all aspects of the fluid loading, heating, and mouthpiece sanitation, as well as providing a docking station for the hand piece 2220 unit and the consumable reservoir 2280. Base station 2250 may also include user interface to provide feedback to the user on the system status and diagnostic analysis results such as, but not limited to fluid level, charging level, sanitation process status, last time device was used.

In other embodiments, a piston pump with check-valves will be used for liquid delivery.

In yet other embodiments, a rotary piston pump will be used for liquid delivery. This pump is known by those in the art, and the piston rotates as it reciprocates, therefore not needing any valves to operate. Reversing the rotation direction of the drive motor will reverse the liquid flow direction.

In still other embodiments diaphragm pumps, gear pumps, or double-action piston pumps will be used for liquid delivery. In the case of double-action piston pumps, when the liquid system is charged, this pump type has the benefit of reciprocating the direction of the liquid flow to the mouthpiece. Charged pneumatic cylinders, hand pump, or rotary pumps may be used to drive the system.

What is claimed is:

1. A method for collecting saliva from the oral cavity of a mammal, said method comprising:
    placing a mouthpiece of a device comprising said mouthpiece in the oral cavity of a mammal, said mouthpiece comprising a chamber defined by front and rear inner walls and a base inner wall of said mouthpiece, said base wall extending between said front and rear inner walls, each of said front and rear inner walls of said chamber comprising a plurality of openings, and a switch disposed in said mouthpiece; and said device further comprising a saliva collection reservoir, a fluid supply reservoir, a pump, and means for directing fluid through said device, wherein said switch is disposed in said mouthpiece at a location sensitive to a biting motion and wherein said switch is activated by biting down on said switch;
    introducing in the oral cavity an agent selected from the group consisting of a saliva sample stimulating agent, and a conglomeration agent;
    activating said switch disposed in said mouthpiece to pump saliva from the oral cavity to the saliva collection reservoir for collection;
    deactivating said pumping of saliva to the saliva collection reservoir after three or more down bites on said switch;
    subsequently pumping fluid from the fluid supply reservoir to the mouthpiece for cleaning or treatment of the oral cavity; and
    analyzing the saliva collected by a method selected from the group consisting of lateral flow technology, microfluid immunoassay, DNA-DNA hybridization, color metrics, photoimaging, gas chromatography, zinc oxide semiconductor sensors, quantitative light fluorescence and quantitative Polymerase Chain Reaction.

2. A method for collecting saliva from the oral cavity of a mammal, said method comprising:
    placing a mouthpiece of a device comprising said mouthpiece in the oral cavity of a mammal, said mouthpiece comprising a chamber defined by front and rear inner walls and a base inner wall of said mouthpiece, said base wall extending between said front and rear inner walls, each of said front and rear inner walls of said chamber comprising a plurality of openings, and a switch disposed in said mouthpiece; and said device further comprising a saliva collection reservoir, a fluid supply reservoir, a pump, and means for directing fluid through said device, wherein said switch is disposed in said mouthpiece at a location sensitive to a biting motion and wherein said switch is activated by biting down on said switch;
    activating said switch disposed in said mouthpiece to pump saliva from the oral cavity to the saliva collection reservoir for collection;
    deactivating said pumping of saliva to the saliva collection reservoir after three or more down bites on said switch; and
    subsequently pumping fluid from the fluid supply reservoir to the mouthpiece for cleaning or treatment of the oral cavity.

3. A method for collecting saliva from the oral cavity of a mammal, said method comprising:
- placing a mouthpiece of a device comprising said mouthpiece in the oral cavity of a mammal, said mouthpiece comprising a chamber defined by front and rear inner walls and a base inner wall of said mouthpiece, said base wall extending between said front and rear inner walls, each of said front and rear inner walls of said chamber comprising a plurality of openings, and a switch disposed in said mouthpiece; and said device further comprising a saliva collection reservoir, a fluid supply reservoir, a pump, and means for directing fluid through said device;
- activating said switch disposed in said mouthpiece to pump saliva from the oral cavity to the saliva collection reservoir for collection;
- deactivating said pumping of saliva to the saliva collection;
- subsequently pumping fluid from the fluid supply reservoir to the mouthpiece for cleaning or treatment of the oral cavity; and
- analyzing the saliva collected by a method selected from the group consisting of lateral flow technology, microfluid immunoassay, DNA-DNA hybridization, color metrics, photoimaging, gas chromatography, zinc oxide semiconductor sensors, quantitative light fluorescence and quantitative Polymerase Chain Reaction.

4. A method for collecting saliva from the oral cavity of a mammal, said method comprising:
- placing a mouthpiece of a device comprising said mouthpiece in the oral cavity of a mammal, said mouthpiece comprising a chamber defined by front and rear inner walls and a base inner wall of said mouthpiece, said base wall extending between said front and rear inner walls, each of said front and rear inner walls of said chamber comprising a plurality of openings, and a switch disposed in said mouthpiece; and said device further comprising a saliva collection reservoir, a fluid supply reservoir, a pump, and means for directing fluid through said device;
- introducing in the oral cavity an agent selected from the group consisting of a saliva sample stimulating agent, and a conglomeration agent;
- activating said switch disposed in said mouthpiece to pump saliva from the oral cavity to the saliva collection reservoir for collection;
- deactivating said pumping of saliva to the saliva collection;
- subsequently pumping fluid from the fluid supply reservoir to the mouthpiece for cleaning or treatment of the oral cavity.

* * * * *